(12) United States Patent
Payne et al.

(10) Patent No.: US 6,322,548 B1
(45) Date of Patent: Nov. 27, 2001

(54) DELIVERY CATHETER SYSTEM FOR HEART CHAMBER

(75) Inventors: Sam G. Payne, Santa Clara; Randy J. Kesten, Mountain View, both of CA (US); Michael Aita, Shorewood, WI (US); Stewart Kume, Belmont, CA (US); Stephen B. Pearce, San Jose, CA (US); Manuel A. Javier, Jr., Santa Clara; Michael H. Rosenthal, Palo Alto, both of CA (US)

(73) Assignee: Eclipse Surgical Technologies, Sunnyvale, CA (US)

( * ) Notice: Subject to any disclaimer, the term of this patent is extended or adjusted under 35 U.S.C. 154(b) by 0 days.

(21) Appl. No.: 09/052,971

(22) Filed: Mar. 31, 1998

Related U.S. Application Data

(63) Continuation-in-part of application No. 08/646,856, filed on May 8, 1996, now abandoned, which is a continuation-in-part of application No. 08/438,743, filed on May 10, 1995, now abandoned.

(51) Int. Cl.[7] ................................................. A61M 31/00
(52) U.S. Cl. ......................................................... 604/500
(58) Field of Search ..................................... 604/500, 506, 604/507, 508, 511, 523, 532, 28, 21

(56) References Cited

U.S. PATENT DOCUMENTS

| | | | |
|---|---|---|---|
| 4,994,033 | 2/1991 | Shockey et al. | 604/101 |
| 5,049,132 | 9/1991 | Shaffer et al. | 604/101 |
| 5,183,470 | 2/1993 | Wettermann | 604/281 |
| 5,213,570 | 5/1993 | VanDeripe | 604/28 |
| 5,213,576 | 5/1993 | Abiuso et al. | 604/96 |

(List continued on next page.)

FOREIGN PATENT DOCUMENTS

| | | | |
|---|---|---|---|
| 9215779 | 2/1993 | (DE) . | |
| 9217693 | 5/1993 | (DE) | A61M/25/00 |
| 0727236 | 8/1996 | (EP) . | |
| 0728494 | 8/1996 | (EP) . | |
| 0818208 | 1/1998 | (EP) | A61M/5/00 |
| WO 94/21237 | 9/1994 | (WO) . | |
| WO 96/30072 | 10/1996 | (WO) . | |
| WO 96/35469 | 11/1996 | (WO) . | |
| WO 97/23526 | 7/1997 | (WO) . | |
| WO 98/19614 | 5/1998 | (WO) . | |
| WO99/22655 | 5/1999 | (WO) . | |
| WO 96/39965 | 12/1996 | (WO) | A61B/17/36 |
| WO 99/22797 | 5/1999 | (WO) | A61M/25/00 |

OTHER PUBLICATIONS

Arras et al., "The Delivery of Angiogenic Factors to the Heart by Microsphere Therapy", *Nat. Biotech.*, 1998; 16:159–162.

(List continued on next page.)

*Primary Examiner*—John D. Yasko
(74) *Attorney, Agent, or Firm*—Heller, Ehrman, White & McAuliffe LLP

(57) ABSTRACT

A delivery catheter system for delivering a substance delivery member into a patient's left ventricle which includes a first delivery catheter with a shaped distal extremity configured to be aligned with or parallel to a longitudinal axis or long dimension of the patient's left ventricle and a second delivery catheter slidably and rotatably disposed within an inner lumen of the first delivery catheter which has a shaped distal shaft section and an inner lumen configured to slidably receive a substance delivery member such as an elongated cannula slidably disposed within a polymer sheath. The shaped distal section of the first delivery catheter is shaped or is shapeable within the patient's heart chamber. The second delivery catheter is advanced out of the inner lumen of the first delivery catheter until the distal end extends out of the port in the distal end of the first delivery catheter and provides a passageway for substance delivery member to engage the endocardial surface at a perpendicular or near perpendicular orientation.

46 Claims, 13 Drawing Sheets

U.S. PATENT DOCUMENTS

| | | | |
|---|---|---|---|
| 5,244,460 | 9/1993 | Unger et al. | 604/53 |
| 5,267,982 | 12/1993 | Sylvanowicz | 604/281 |
| 5,269,326 | 12/1993 | Verrier | 128/642 |
| 5,302,706 | 4/1994 | Smith | 536/23.1 |
| 5,318,957 | 6/1994 | Cid et al. | 514/8 |
| 5,328,470 | 7/1994 | Nabel et al. | 604/101 |
| 5,419,777 | 5/1995 | Hofling | 604/264 |
| 5,431,649 | 7/1995 | Mulier et al. | 606/41 |
| 5,464,395 | 11/1995 | Faxon et al. | 604/96 |
| 5,571,151 | 11/1996 | Gregory | 607/88 |
| 5,634,899 | 6/1997 | Shapland et al. | 604/51 |
| 5,702,359 | 12/1997 | Hofmann et al. | 604/20 |
| 5,766,163 | 6/1998 | Mueller et al. | 606/7 |
| 5,836,905 | 11/1998 | Lemelson et al. | 604/21 |
| 5,840,059 | 11/1998 | March et al. | 604/53 |
| 6,045,565 | 4/2000 | Ellis et al. | 606/167 |

OTHER PUBLICATIONS

Dichek et al., "Seeding of Intravascular Stents With Genetically Engineered Endothelial Cells", *Circulation*, 1989; 80:1347–1353.

Flugelman et al., "Low Level In Vivo Gene Transfer Into the Arterial Wall Through a Perforated Balloon Catheter", *Circulation*, 1992; 85:1110–1117.

French et al., Direct In Vivo Gene Transfer Into Porcine Myocardium Using Replication–Deficient.

Goldsmith, "Tomorrow's Gene Therapy Suggests Plenteous, Patent Cardiac Vessels", *JAMA*, 1992; 268–3285–3286.

Guzman et al., "Efficient Gene Transfer Into Myocardium by Direct Injection of Adenovirus Vectors", *Circulation Research*, 1993; 73:1202–1207.

Kirshenbaum et al., "Detection of Exogenous Gene Expression in Live Adult Ventricular Myocytes After Adenoviral Gene Delivery", Unknown, 1994; 2124–2125.

Kirshenbaum et al., "Highly Efficient Gene Transfer into Adult Ventricular Myocytes by Recombinant Adenovirus", *J. Clin.Invest.*, 1993;82:381–387.

Leclerc et al., "Percutaneous Arterial Gene Transfer in a Rabbit Model", *J. Clin. Invest.*, 1992; 90:936–944.

Li et al., "Percutaneous Transluminal Gene Transfer Into Canine Myocardium In Vivo by Replication–Defective Adenovirus", 1995; 30:97–105.

Lin et al., "Expression of Recombinant Genes in Myocardium In Vivo After Direct Injection of DNA", *Circulation*, 1990; 82:2217–2221.

Lynch et al., "Long–Term Expression of Human Adenosine Deaminase in Vascular Smooth Muscle Cells of Rats: A model for gene therapy", *Proc. Natl. Acad. Sci. USA*, 1992;89:1138–1142.

March et al., "Pharmacokinetics of Adenoviral Vector–Mediated Gene Delivery to Vascular Smooth Muscle Cells: Modulation by Poloxamer 407 and Implications for Cardiovascular Gene Therapy", *Human Gene Therapy*, 1995; 6:41–53.

Nabel et al., "Recombinant Platelet–Derived Growth Factor B Gene Expression in Porcine Arteries Induces Intimal Hyperplasia In Vivo", *J. Clin. Invest.* 1993; 91:1822–1829.

Nabel et al., "Site–Specific Gene Expression in Vivo by Direct Gene Transfer into the Arterial Wall", *Science*, 1990; 249:1285–1288.

O'Brien et al., "New Approaches for Gene Transfer in the Myocardium", *Circulation*, 1991; 83:2133–2136.

Schumacher et al., "Induction of Neoangiogenesis in Ischemic Myocardium by Human Growth Factors", *Circulation*, 1998; 97:645–650.

Siegfried, "Perspectives in Gene Theraphy with Recombinant Adenoviruses", *Exp. Clin. Endocrinol.*, 1993; 7–11.

Tice et al., "Getting to the Heart of Growth Factor Delivery", *Nat. Biotech.*, 1998; 16:134.

Wilson et al., Ex Vivo Gene Therapy of Familial Hypercholesterolemia, *Hum. Gene Ther.*, 1992; 3:179–222.

Wilson et al., "Implanatation of Vascular Grafts Lined with Genetically Modified Endothelial Cells", *Science*, 1989; 244:1344–1346.

International Searching Authority communication, "International Search Report", dated May 12, 2000.

DELIVERY CATHETER SYSTEM FOR HEART CHAMBER

RELATED APPLICATIONS

This application is a continuation-in-part of application Ser. No. 08/646,856, filed on May 8, 1996, now abandoned entitled SYSTEM AND METHOD FOR TREATING OR DIAGNOSING HEART TISSUE, which is a continuation-in-part of application Ser. No. 08/438,743, filed on May 10, 1995, now abandoned entitled DELIVERY SYSTEM AND METHOD FOR MYOCARDIAL REVASCULARIZATION, both of which are incorporated herein in their entirety by reference.

BACKGROUND OF THE INVENTION

This invention relates to the diagnosis and/or treatment of a patient's heart and particularly to the delivery of therapeutic or diagnostic devices and agents to a patient's heart tissue from within the patient's heart chamber.

Coronary artery disease affects the lives of millions of patients worldwide. Many therapies are available for atherosclerosis, including CABG surgery to bypass blocked arteries, PTCA interventions to attempt to restore patency, stents that also attempt to maintain patency, atherectomy to remove the collected plaque, and a number of pharmacological approaches that attempt to reduce the effects of narrowing of vessel lumens, by the stenosis, by reducing the amount of plaque or by altering the hemodynamic characteristics of the patient's blood. While the aforesaid procedures provide well known clinical improvements, none provide a fully satisfactory long term therapy. The presently available pharmacological therapies are of limited value. Ideally, a non-invasive pharmacological or genetic therapy would facilitate reperfusion of the ischemic myocardium, either by restoring patency, or by creating new blood vessels to supply the ischemic region with additional oxygenated blood.

A number of different substances and techniques are known for attempting to treat coronary artery disease by the administration of a therapeutic substance to a patient. One common method of administration is systemic administration. For example, EPO Application EP 314105 discloses the oral administration or intramuscular injection of an "angiogenesis enhancer." U.S. Pat. No. 5,480,975 discloses treating hypoxic tissue damage by local or topical administration of a transition metal compound to induce VEGF expression, either by local administration or topical application. The indirect nature of these routes of administration are generally less desirable and not universally applicable to all forms of substances that might be used to treat ischemic myocardium.

Using a catheterization procedure to deliver a substance to the vessels in the vicinity of the stenosis is also known. For example, PCT Application WO 9723256 discloses the percutaneous delivery of an angiogenic factor to a vessel wall through the lumen of a catheter. The distal end of the catheter is provided with infusion ports that engage the vessel wall when the catheter is expanded, and infusion may be enhanced by providing needles or other penetrating elements. U.S. Pat. No. 5,681,278 discloses treating vascular thrombosis and angioplasty restenosis by administering a bioactive agent to an extravascular treatment site, particularly introducing such an agent proximally adjacent to the exterior of a coronary artery. U.S. Pat. No. 5,698,531 discloses site specific installation of cells or the transformation of cells by delivering proteins by catheterization to discrete blood vessel segments wherein the agent is situated on the walls of the blood vessel or perfused in the tissue of the vessel. U.S. Pat. No. 5,523,092 discloses an indwelling catheter for localized delivery of a substance into a tissue conduit without disrupting the fluid flow. U.S. Pat. No. 5,244,460 discloses the intracoronary arterial delivery of a blood vessel growth promoting peptide periodically over several days. None of these references, however, address the provision of a substance directly into the myocardial tissue.

Recent advances in biotechnology have shown great promise for treating coronary artery disease. In *Circulation* 1998, 97:645–650, Schumacher et al. report treating coronary heart diseases using human growth factor FGF-I (basic fibroblast growth factor) to induce neoangiogenesis in ischemic myocardium. The FGF-I was administered during a CABG procedure by injection into the myocardium distal to the IMA/LAD anastamosis and close to the LAD. The results reported demonstrate the efficacy of FGF-I treatment. However, administration by direct injection during surgery is less than optimal because it is as invasive to the patient as a CABG procedure. In addition, at least one fibroblast growth factor has also been delivered using a microparticle carrier delivered to an artery via a catheter in a non-ischemic model, as reported in *Nature Biotechnology* 1998; 16:134 and 159–160. The intra-arterial delivery of microparticles produced positive results, but was chosen so that the surrounding tissue would be undamaged. The article indicates that noninvasive techniques to deliver genes into peripheral ischemic myocardium tissue are presently unavailable.

Targeted delivery of therapeutic or diagnostic devices and/or agents is a desirable but often difficult task. For therapeutic and diagnostic devices the advantages include shorter and less traumatic procedures and for therapeutic and diagnostic agents the benefits include more efficient use of the agent and the limitation of the agent action to a desired region. Whether the delivery of a therapeutic or diagnostic device to a desired region of a patient's heart tissue from within the heart chamber thereof is successful and efficient is frequently the result of the physician's skill which can vary considerably from physician to physician and from day to day with the same physician. Accurate delivery of various substances to the tissue of a patient's heart wall can be a function of the same physician skill. Additionally, successful and effective substance delivery can also be a function of minimizing systemic loss, keeping the substance within the desired region, timing and ensuring a sufficient quantity of substance in the desired area for sufficient period of time to achieve the desired therapeutic or diagnostic effect.

Copending application Ser. No. 08/483,512, filed on Jun. 7, 1995, entitled THERAPEUTIC AND DIAGNOSTIC AGENT DELIVERY, describes a method and system for delivering a therapeutic or diagnostic agent by first forming a channel in a heart wall from within a heart chamber defined by the wall and then delivering or depositing the agent within the channel. Reference is made to the use of a laser to form the channel, particularly in conjunction with a transmyocardial revascularization procedure. The application (Ser. No. 08/483,512) is hereby incorporated herein by reference in its entirety. Agents described in Ser. No. 08/483,512 included vascular endothelial growth factor (VEGF), acidic and basic fibroblast growth factors (aFGF, bFGF), angiogenin, nitric oxide, prostaglandin, prostaglandin synthase and other prostaglandin synthetic enzymes and isoforms of superoxide dismutase and other antioxidant proteins.

Coronary artery disease is also successfully treated by transmyocardial revascularization (TMR) alone, using methods and apparatus such as those disclosed in U.S. Pat. Nos. 5,380316, 5,389,096 and 5,54,152. Using intraoperative, minimally invasive or percutaneous techniques, energy is delivered directly to the myocardium in the ischemic area and as a result, a focal injury occurs. This focal injury is typically in the form of a small "channel" formed by a laser. It is believed that the focal injury acts to stimulate subsequent neovasculogenesis. Moreover, in addition to the reperfusion of the ischemic region, there is evidence that the disruption of certain afferent nerves in the tissue and other effects provides acute and chronic reduction in angina pain.

Suitable means for creating a site for angiogenesis were referenced in copending application Ser. No. 08/078,443, filed on Jun. 15, 1993 (Aita et al.), which is incorporated herein in its entirety. The application describes an intravascular system for myocardial revascularization which is introduced percutaneously into a peripheral artery and advanced through the patient's arterial system into the left ventricle of the patient's heart. The procedure affects only the endocardium and the myocardium from within the left ventricle. This procedure eliminates the need of the prior intraoperative procedures to open the chest cavity and to penetrate through the entire heart wall in order to form the channel through the endocardium into the myocardium.

While the percutaneous method and system for introducing therapeutic and diagnostic agents into a patient's heart wall as described in Ser. No. 08/483,512 represented a substantial advance, one of the difficulties with the procedure was that it was difficult to ensure delivery of all of the agent into the channel and keeping the agent within the channel for a sufficient period until the desired therapeutic or diagnostic affect occurred. There exists, therefore, a need for improved apparatus and improved techniques that will permit the adjunctive delivery of substances into localized areas within the myocardium efficaciously, efficiently and in a manner that can enjoy widespread adoption by cardiac surgeons and interventional cardiologists. There also exists a long felt, yet unsolved need for methods and apparatus that permit the localized introduction of a substance into the myocardium directly, either during an intraoperative procedure or percutaneously. What has been needed is an improved delivery system and method for delivering a therapeutic or diagnostic device or agent into heart tissue from within the patient's heart chamber, particularly to provide access to all or substantially all of the endocardial surface from within the heart chamber for delivery of such agents and devices. The present invention satisfies these and other needs.

SUMMARY OF THE INVENTION

The present invention is directed to a system for delivering an elongated therapeutic or diagnostic device or agent into the wall of a patient's heart from within a chamber defined by the heart wall. The system of the invention has the capability to access tissue in the endocardial, myocardial, and epicardial layers of the heart wall, in addition to other areas of the heart. The invention provides access to a wide region of the patient's endocardial lining and the tissue beneath it. The system also accurately places and effectively holds the distal end of the system at one or more desired locations within the patient's heart chamber at a desired orientation, e.g. perpendicular or near perpendicular, with respect to the patient's endocardium. The perpendicular or near perpendicular orientation of the distal extremity of the cannula or other device with respect to the endocardial surface of the heart chamber is most desirable. As used herein the terms "normal" and "perpendicular" shall include variations of up to 30° from a normal or perpendicular orientation.

The delivery catheter system of the invention generally includes a first guiding or delivery catheter which has a relatively straight main shaft section and a shaped distal shaft section which is configured to have a discharge axis selected so that it is generally aligned with or parallel to the longitudinal axis of the patient's left ventricle. The discharge axis is herein defined to be the longitudinal axis of the most distal segment of the catheter described. The system also generally includes a second guiding or delivery catheter slidably and rotatably disposed within an inner lumen of the first delivery catheter and provided with a shaped distal section configured to have a discharge axis with a desired orientation.

The system of the invention also has substance delivery member for delivery of a therapeutic or diagnostic agent which is disposed within the inner lumen of the second delivery catheter. The substance delivery member is configured so it can be advanced into the wall of the patient's heart. The member preferably has an injector, which may be a syringe or other suitable device, provided on the proximal end of a cannula to deliver the diagnostic or therapeutic agent in a carrier fluid or gel or in solid form through the inner lumen of the cannula into the tissue of the patient heart wall.

Preferably, the distal extremity of the substance delivery member which extends out the distal end of the second delivery catheter has sufficient rigidity to penetrate the tissue of the heart, and be self-supporting within the environment of the heart chamber. Generally, the distal portion of the substance delivery member is considered as being "self supporting" if a force of at least 4 grams, preferably at least 8 grams, is required to deflect the free end of a cantilevered specimen 0.5 inch (12.7 mm) in length (span length) of cannula a distance of one millimeter. A sheath surrounding the cannula can also act to provide support.

In one preferred embodiment, an injector or syringe member containing a therapeutic or diagnostic agent is incorporated into the distal extremity of an elongated cannula slidably disposed within the inner lumen of the second delivery catheter for delivery of the agent into the heart wall. The agent may be in a carrier fluid or gel, or may be in a solid form. The injector is actuated at the proximal end of the delivery system which extends out of the patient. The injector may be set up for a single or multiple doses.

The location of the distal end of the substance delivery member within the heart chamber, and particularly with respect to the endocardial surface, can be detected fluoroscopically by providing a radiopaque marker on the distal extremity of the delivery member, either or both of the polymer sheath or elongated cannula, and optionally, either or both of the delivery catheters. The radiopaque marker can be made from a suitable metal, such as gold, platinum or tantalum, or the like, or a material such as $BaSO_4$ or Bismuth can be added to the material that forms the polymer sheath, or the first or second delivery catheter. The use of dye injections through a port in the distal end of first or the second delivery catheter may be employed to further facilitate the location of the distal end of these catheters. Other means such as a variety of proximity detectors, including ultrasonic proximity detectors, may be employed to detect contact between the distal end of the substance delivery member or the delivery catheters and the endocardium.

In accordance with one presently preferred embodiment of the present invention, the first delivery catheter has proximal and distal ends, a port in the distal end and an inner lumen extending within the catheter to the port in the distal end. The first delivery catheter has a relatively straight main shaft section and a preshaped distal section configured to point in a direction so that the discharge axis of this catheter is aligned with or parallel or near parallel to the longitudinal axis of the left ventricle or other chamber into which it is inserted. For many applications the first delivery catheter is about 90 to about 130 cm, preferably about 100 to about 120 cm in length.

The first delivery catheter preferably has a main shaft section and a shaped distal section with a first segment and a second segment which provide a discharge axis approximating the longitudinal axis or long dimension of the heart chamber. The first segment of the distal shaft section of the first delivery catheter should be at an angle of about 95° to about 160°, preferably about 100° to about 150° with respect to a proximally adjacent second segment of the distal shaft section. The proximally adjacent second segment should be at an angle of about 95° to about 160°, preferably about 100° to about 150° with respect to either the proximally adjacent main shaft section or a third segment of the distal shaft section proximally adjacent to the second segment. If there is a third segment of the distal section, it is at an angle of about 110° to about 170°, preferably about 120° to about 150° with respect to proximally adjacent main shaft section. The first and second segments should each be about 0.5 to about 5 cm, preferably about 0.5 to about 4 cm in length, with the total length of the shaped distal section with two segments being about 2 to about 6 cm. If the distal section has a third segment, it should have a length of about 1 to about 5 cm, preferably about 2 to about 4 cm. The length of the shaped distal section with three segments should be about 3 to about 8 cm, preferably about 4 to about 7 cm.

In another embodiment, the shaped distal section of the first delivery catheter has a single angled segment which provides a discharge axis approximating the longitudinal axis or long dimension of the heart or other chamber into which it is disposed. In this embodiment the single angled segment of the distal shaft section has a length of about 2 to about 8 cm, preferably about 4 to about 6 cm and is at an angle of about 95° to about 160°, preferably about 100° to about 140° with respect to a proximally adjacent portion of the main shaft section.

The second delivery catheter of the invention is longer than the first delivery catheter, and is slidably and preferably rotatably disposed within inner lumen of the first delivery catheter. The second delivery catheter likewise has proximal and distal ends, a port in the distal end and an inner lumen extending within the second delivery catheter to the port in the distal end. The second delivery catheter has a relatively straight main shaft section and a distal section which is at an angle of about 80° to about 140°, preferably about 90° to about 120° with respect to the main shaft section thereof. The second delivery catheter should be at least 10 cm longer, preferably about 15 to about 50 cm longer, than the first delivery catheter and is about 100 to about 150 cm, preferably about 110 to about 140 cm in length. The shaped distal section of the second delivery catheter should have a radius of curvature of about 2 to 30 mm, preferably about 4 to about 20 mm between the main shaft section and the exit or discharge axis through the port in the distal end of the shaped distal section. The length of the shaped distal section of the second delivery catheter is about 0.5 to about 4 cm, preferably about 1 to about 3 cm. The angles of the various segments of the distal section of the first and second delivery catheters facilitate directing the operative distal end of an elongated substance delivery member, which is slidably disposed within the inner lumen of the second delivery catheter, toward the region of the endocardium where the procedure is to be performed at an orientation that is preferably perpendicular or near perpendicular with the endocardial surface of the patient's heart wall.

The second delivery catheter is rotatably and slidably disposed within the inner lumen of the first delivery catheter to facilitate the desired placement and orientation of the shaped distal section of the second delivery catheter within the left ventricle, e.g. substantially normal to the endocardium. In this manner an elongated cannula slidably disposed within the inner lumen of the second delivery catheter or the injector at the distal extremity of the second delivery catheter is properly oriented with respect to the endocardial surface of the heart chamber in order to effectively be inserted into the heart wall. The elongated cannula may also be disposed within a polymer sheath which is slidably disposed with in the inner lumen of the second delivery catheter. The polymer sheath has a proximal end and a distal end, preferably with at least one penetration limiter disposed on the distal end of the polymer sheath. The sheath protects the tip from inadvertently damaging tissue or other parts of the catheter delivery system.

The distal sections of the first and second delivery catheters are preferably preformed into a desired shape so that they will provide a desired orientation for the delivery system when they extend into the patient's heart chamber. However, the catheters may alternatively be provided with control lines, pull wires, or other suitable means (e.g., a shape memory or a superelastic or pseudoelastic NiTi element) to deflect or otherwise shape the distal sections of the catheters once the distal extremity of the delivery system extends into the heart chamber. The system of the present invention essentially provides access at a desired normal or near normal orientation to the entire semi-conical inner surface of the free wall defining part the patient's heart chamber and the intraventricular septum.

The first and second delivery catheters are preferably relatively stiff catheters so that the position of the cannula or other substance delivery member will be maintained during the procedure even though the heart is beating and blood is flowing within the chamber. The delivery catheters, and particularly the first delivery catheter, are preferably provided with relatively stiff proximal and shaped distal sections with a more flexible intermediate section which is configured to be disposed within the patient's aortic arch during the procedure as described in copending application Ser. No. 08/813,503 entitled CATHETER WITH FLEXIBLE INTERMEDIATE SECTION and filed on Mar. 7, 1997, which is incorporated herein by reference.

In a presently preferred embodiment of practicing the method of the invention, the first delivery catheter of the delivery catheter system is introduced into a peripheral artery, such as the femoral artery, and advanced through the patient's arterial system until the distal end of the first catheter is disposed within the patient's left ventricle. The position of the first delivery catheter is adjusted by the physician under fluoroscopic observation or other techniques until its distal tip is oriented generally along or parallel to the longitudinal axis of the left ventricle. The second delivery catheter is advanced through the previously introduced first delivery catheter which has a distal end appropriately positioned within the left ventricle. The distal end of the second delivery catheter is then adjusted under flouroscopic visualization, or the like, until it is oriented perpendicular to the wall of the heart adjacent the tissue to be treated. The substance delivery member is then advanced distally until contact is made with the tissue of the heart wall. The elongated cannula is then advanced into the tissue to be treated, and the diagnositic or therapeutic substance injected with a syringe through the elongated cannula and out its distal end into the tissue to be treated.

The system of the invention has the capability to access tissue in the endocardial, myocardial, and epicardial layers of the heart wall, in addition to other areas of the heart. The invention provides access to a wide region of the patient's endocardial lining and the tissue beneath it which defines the heart chamber. The system also accurately places and effectively holds the distal end of the system at one or more desired locations within the patient's heart chamber at a desired orientation, e.g. perpendicular or near perpendicular, with respect to the patient's endocardium.

These and other advantages of the invention will become more apparent from the following detailed description of the invention, when taken in conjunction with the accompanying exemplary drawings.

DETAILED DESCRIPTION OF THE INVENTION

Figure 1:
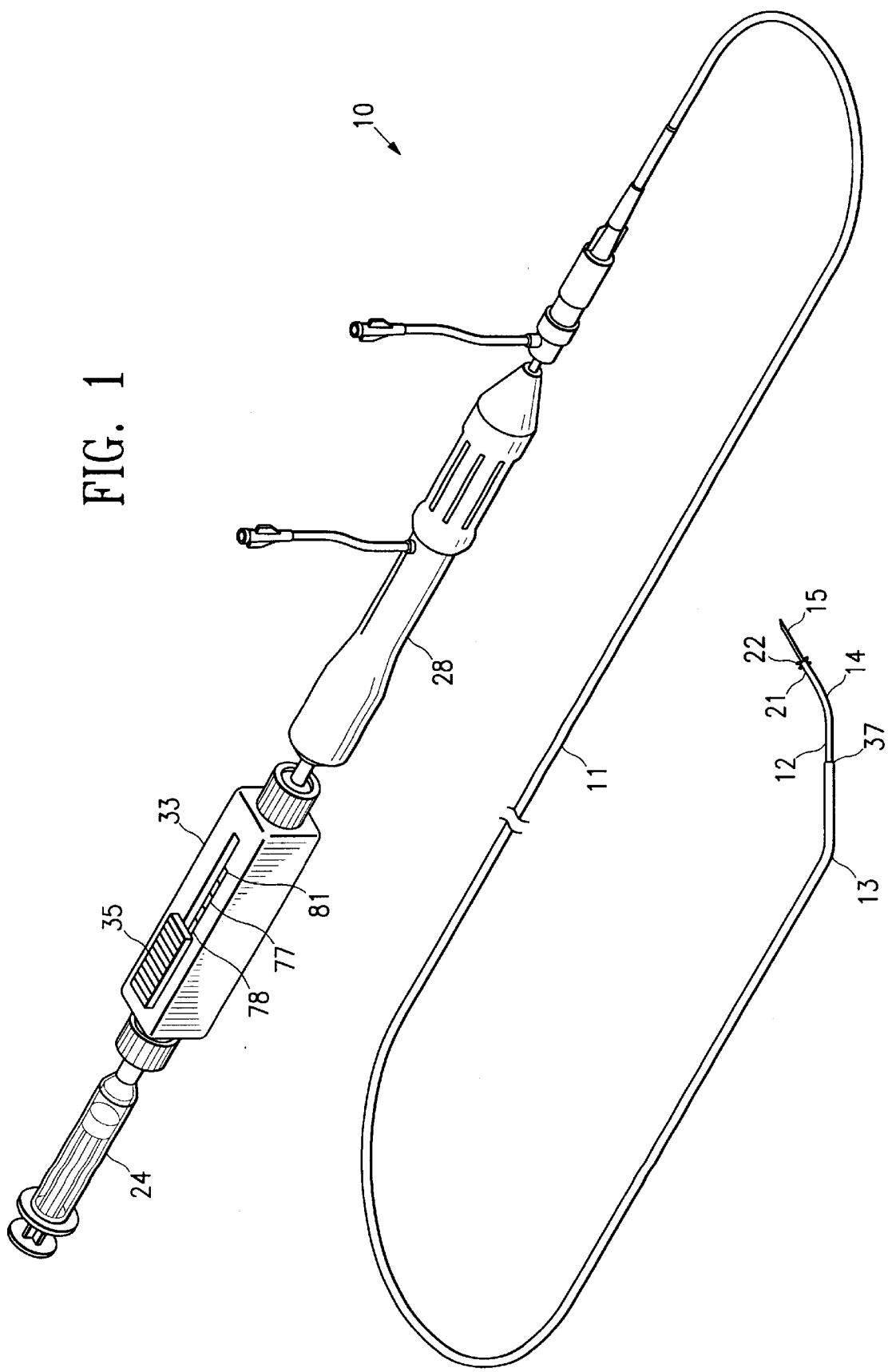
FIG. 1 is a perspective view of an embodiment of the present invention.

FIG. 1 illustrates an embodiment of the invention which is a delivery catheter system 10 having a first delivery catheter 11 and a second delivery catheter 12 which is longer than the first delivery catheter and slidably and 20 rotatably disposed within the first delivery catheter. Preferably the first delivery catheter 11 has an angled distal shaft section 13 and the second delivery catheter 12 has an angled distal shaft section 14. The angled distal shaft sections 13 and 14 of the delivery catheters 11 and 12 can be proximally manipulated and positioned relative to each other by translation and rotation to achieve a desired position and angular orientation during a procedure.

Referring to FIGS. 1 and 2, and FIGS. 9–11, a substance delivery member 15, which is preferably an elongated cannula 16 slidably disposed within a polymer sheath 17, is slidably disposed within the second delivery catheter 12 such that a distal end 18 of the polymer sheath can extend beyond a distal end 21 of the second delivery catheter 12 and engage the desired tissue of a heart wall. Preferably, at least one penetration limiter 22 is operatively disposed on the distal end of the polymer sheath 18. A proximal end 23 of the elongated cannula 16 is in fluid communication with an injector 24 which forces a therapeutic or diagnostic substance 25 from the injector into the proximal end of the elongated cannula, out the distal end 26 of the elongated cannula, and into tissue to be treated.

Figure 2:
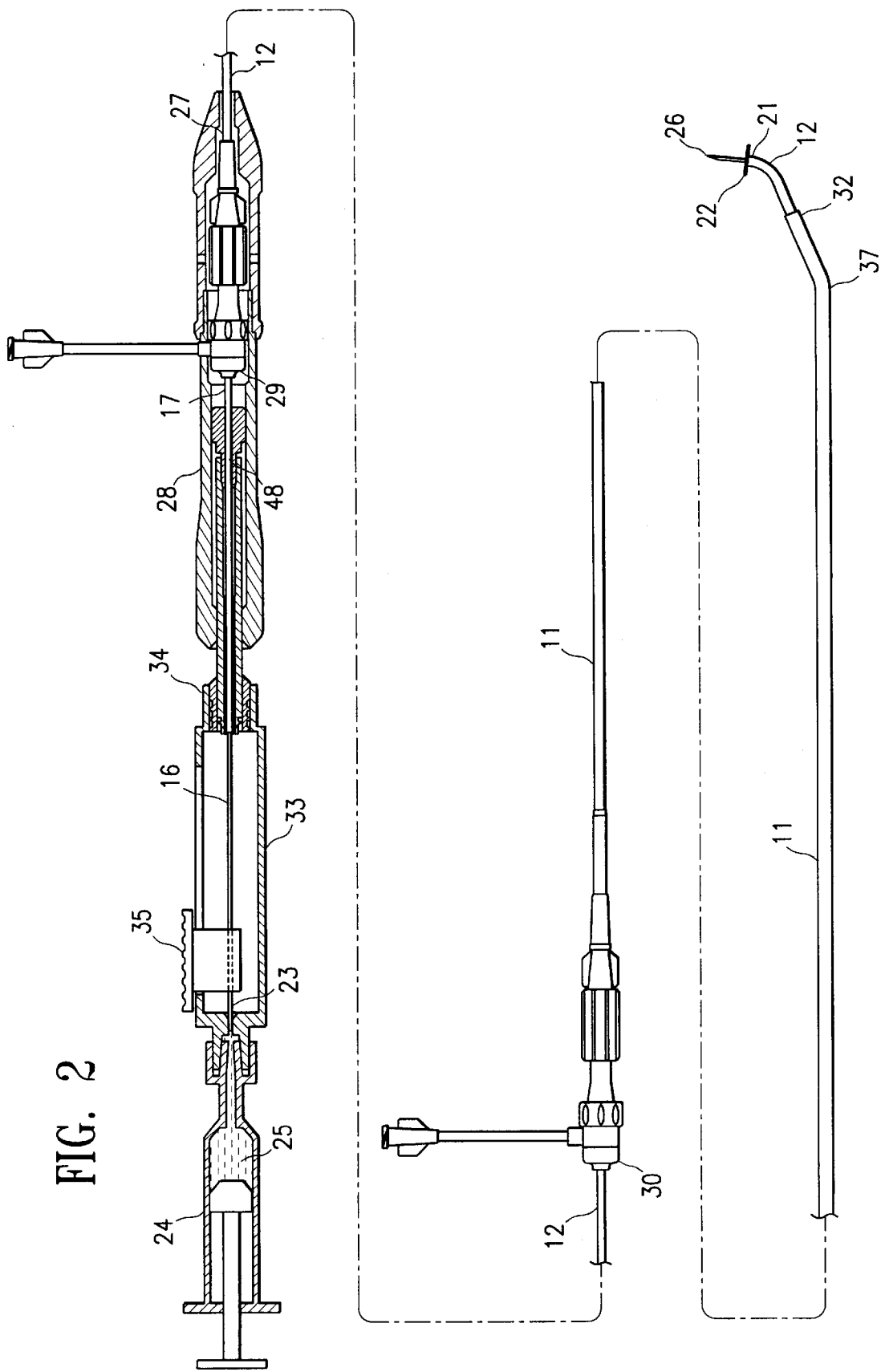
FIG. 2 is an elevational view of the proximal assembly.

Referring to preferred embodiments of the invention illustrated in FIG. 1 and FIG. 2, the proximal end 27 of the second delivery catheter 12 is fixed within the proximal controller 28 by a proximal hemostasis member 29 which is disposed within the proximal controller, and mechanically engages and seals the proximal end 27 of the second delivery catheter and the polymer sheath 17. Thus, fluids that are forced into the distal end 21 of the second delivery catheter under pressure, such as blood, can not leak out the proximal end 27 of the second delivery catheter at the point where the polymer sheath exits said proximal end of the second delivery catheter. However, axial movement between the polymer sheath 17 and the second delivery catheter 12 is still provided for, notwithstanding the seal therebetween. The first delivery catheter 11 is sealingly engaged to the proximal end 27 of the second delivery catheter by a distal hemostasis member 30.

Because the second delivery catheter 12 is fixed to the proximal controller 28 by the proximal hemostasis member 29, movement of the proximal controller 28 relative to the first delivery catheter 11 moves the first delivery catheter in relation to the second delivery catheter. By such relative movement, the angle that the distal end 21 of the second delivery catheter makes with the distal end 32 of the first delivery catheter can be adjusted. This is possible because the distal end 21 of the second delivery catheter will conform to some degree or a large degree, depending on the relative stiffness of the two delivery catheters 11 and 12, to the shape and direction of the distal end 32 of the first delivery catheter 11.

The illustrated embodiment of the invention also has an advancement controller 33 which is located proximally and slidably coupled to the proximal controller 28. The polymer sheath 17 is attached at the distal end 34 of the advancement controller 33 and the elongated cannula is attached to a slider 35 which remains stationary with respect to the advancement controller 33, unless deliberately moved relative thereto. Therefore, movement of the advancement controller 33 in relation to the proximal controller 28 moves the polymer sheath 17 and elongated cannula 16 in relation to the second delivery catheter 12. The slider 35 is mechanically attached to the proximal end 23 of the elongated cannula 16 and is slidably disposed upon the advancement controller 33.

Translating the slider 35 relative to the advancement controller 33 proportionally translates the elongated cannula 16 in relation to the polymer sheath 17 which surrounds at least a substantial portion of the elongated cannula. In this way, once the distal end 21 of the second delivery catheter 12 is properly positioned adjacent tissue to be treated by translation and rotation of the first delivery catheter 11 and second delivery catheter, the distal end of the polymer sheath 18 can be advanced distally to contact the tissue by movement of the advancement controller relative to the proximal controller. The distal end of the elongated cannula 26, which preferably includes a sharp 36, can then be extended into the tissue by distally advancing the slider 35 relative to the advancement controller 33, and a desired therapeutic substance injected into the tissue by the injector 24.

Figure 3:
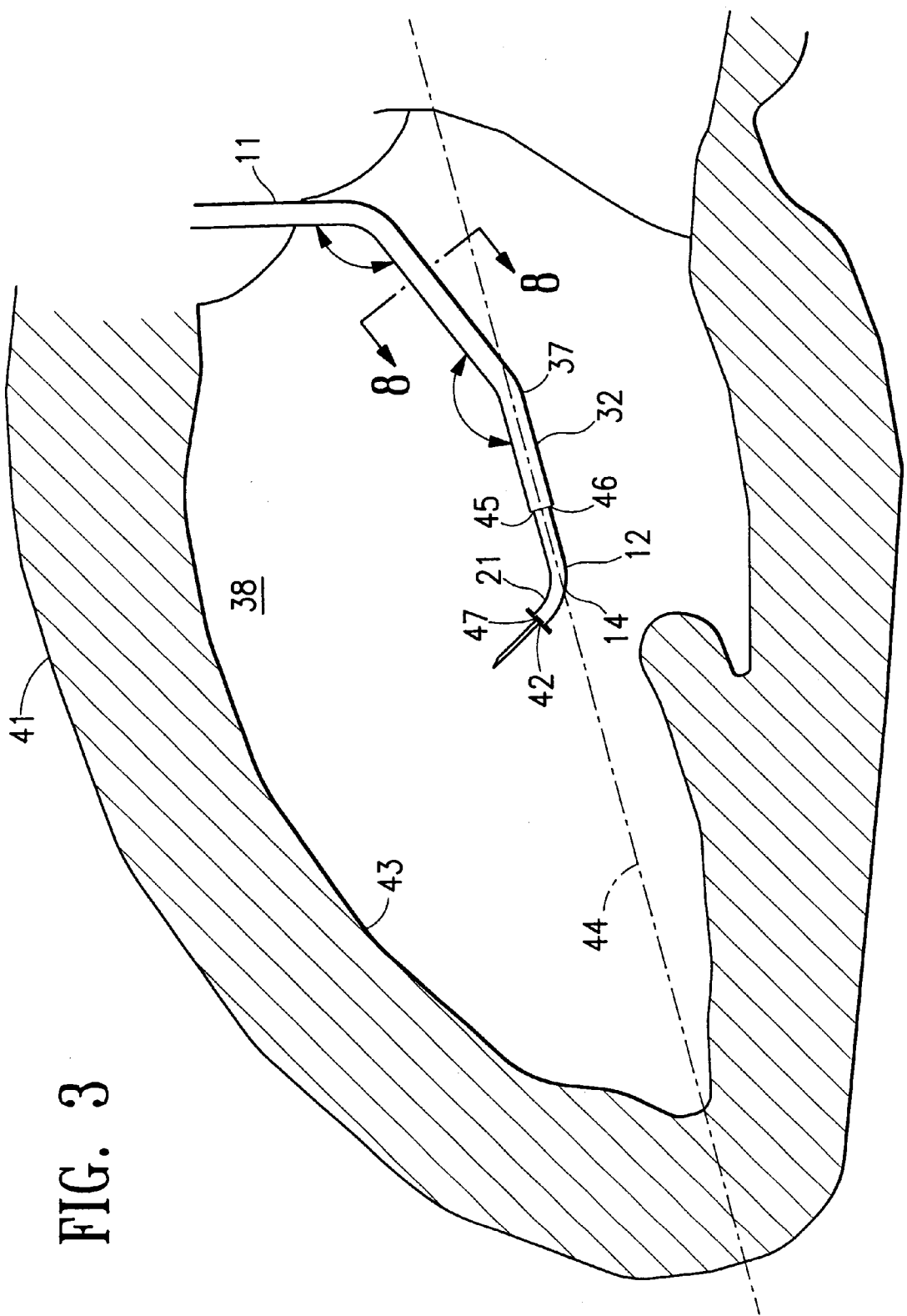
FIG. 3 is an elevational view of a delivery catheter system embodying features of the invention with the distal extremity of the system disposed within the patient's left ventricle, which is seen in a left lateral cutaway view.

FIG. 3 schematically illustrates a distal end 37 of one presently preferred embodiment of the delivery catheter system 10 of the invention disposed within the left ventricle 38 of a patient's heart 41. Once the distal end 21 of the second delivery catheter 12 is properly positioned adjacent tissue surface 43 in the heart 41 by translation and rotation of the first delivery catheter 11 and second delivery catheter, the distal end of the polymer sheath 18 can be advanced to contact the tissue surface by movement of the advancement controller 33 relative to the proximal controller 28. The distal end of the elongated cannula 26 can then be extended into the tissue by distally advancing the slider 35 relative to the advancement controller 33, and a therapeutic or diagnostic substance injected into the tissue by the injector 24.

In a presently preferred method of the invention, the first delivery catheter 11 is first introduced into the patient's arterial system preferably by means of the Seldinger technique through the femoral artery and advanced through the patient's arterial system including the aorta until a distal end 32 of the first delivery catheter 11 is disposed at a desired location within the left ventricle 38 generally aligned with or parallel to the longitudinal axis 44 of the left ventricle 38. The second delivery catheter 12 and the polymer sheath 17 which at least partially surrounds the elongated cannula 16, or some other suitable substance delivery member, may then be advanced together or sequentially through the inner lumen 45 of the first delivery catheter 11 into the left ventricle 38. The second delivery catheter 12 is advanced out of, rotated within or withdrawn into the inner lumen 45 of the first delivery catheter to orient the distal end 21 of the second delivery catheter 12 toward a desired region within the left ventricle 38 where the procedure is to be performed.

The distal shaft section 14 of the second delivery catheter 12 is preshaped so that it forms the desired shape when exiting the port 46 in the distal end of the first delivery catheter 32. The distal end 18 of the polymer sheath may then be advanced through the inner lumen of a second delivery catheter 42 and out a port 47 in the distal end 21 thereof until contact is achieved with the tissue surface 43. Preferably pressure is applied to the polymer sheath 17 from its proximal end 48 so as to maintain contact with the tissue of the heart 41 when deploying the sharp 36 of the elongated cannula 16. The axial force applied to the proximal end 48 of the polymer sheath 17 via the advancement controller 33 is preferably sufficient to ensure contact with tissue of the heart wall 41, but the force should not exceed the level which will cause a distal tip 18 of the polymer sheath 17 surrounding the elongated cannula 16 to mechanically penetrate heart tissue 41. Preferably, penetration of the distal end 18 of the polymer sheath is prevented at least in part by at least in part penetration limiter 22 disposed on the distal end of the polymer sheath. The penetration limiters 22 are preferably composed of shape memory or psuedoelastic alloy, such as Nitinol, however any suitable material having the appropriate mechanical characteristics can be used.

Once contact is made with the tissue of the area to be treated, the elongated cannula 16 having a sharp 36 may be advanced into the tissue to the desired depth by advancing the slider 35 which is slidably housed in the advancement controller 33 and which is mechanically coupled to the proximal end 23 of the elongated cannula 16. Once the distal tip 51 of the elongated cannula 16 is in position, the therapeutic or diagnostic substance 25 is delivered out of the distal tip 51 by activating the injector 24 which forces the substance into the proximal end 23 of the elongated cannula and out of the distal tip 51 into the tissue to be treated. The elongated cannula 16 may then be withdrawn and the procedure repeated in another location until the desired amount of substance 25 has been delivered. An alternative method would incorporate an embodiment of the invention whereby the injector 24 and substance to be delivered 25 are disposed upon the distal end 37 of the delivery catheter system 10 and the therapeutic or diagnostic substance 25 is injected directly into the tissue by remote activation of the injector.

Generally, the overall length of the polymer sheath 17 and the elongated cannula 16 are longer than the second delivery catheter 12 and are preferably configured to extend out of the second delivery catheter a distance of up to about 15 cm, preferably about 4 to about 10 cm to perform the desired therapeutic or diagnostic procedure. The polymer sheath 17 and elongated cannula 16 should have the flexibility required to pass through the inner lumen 42 of the second delivery catheter 12.

Figure 4:
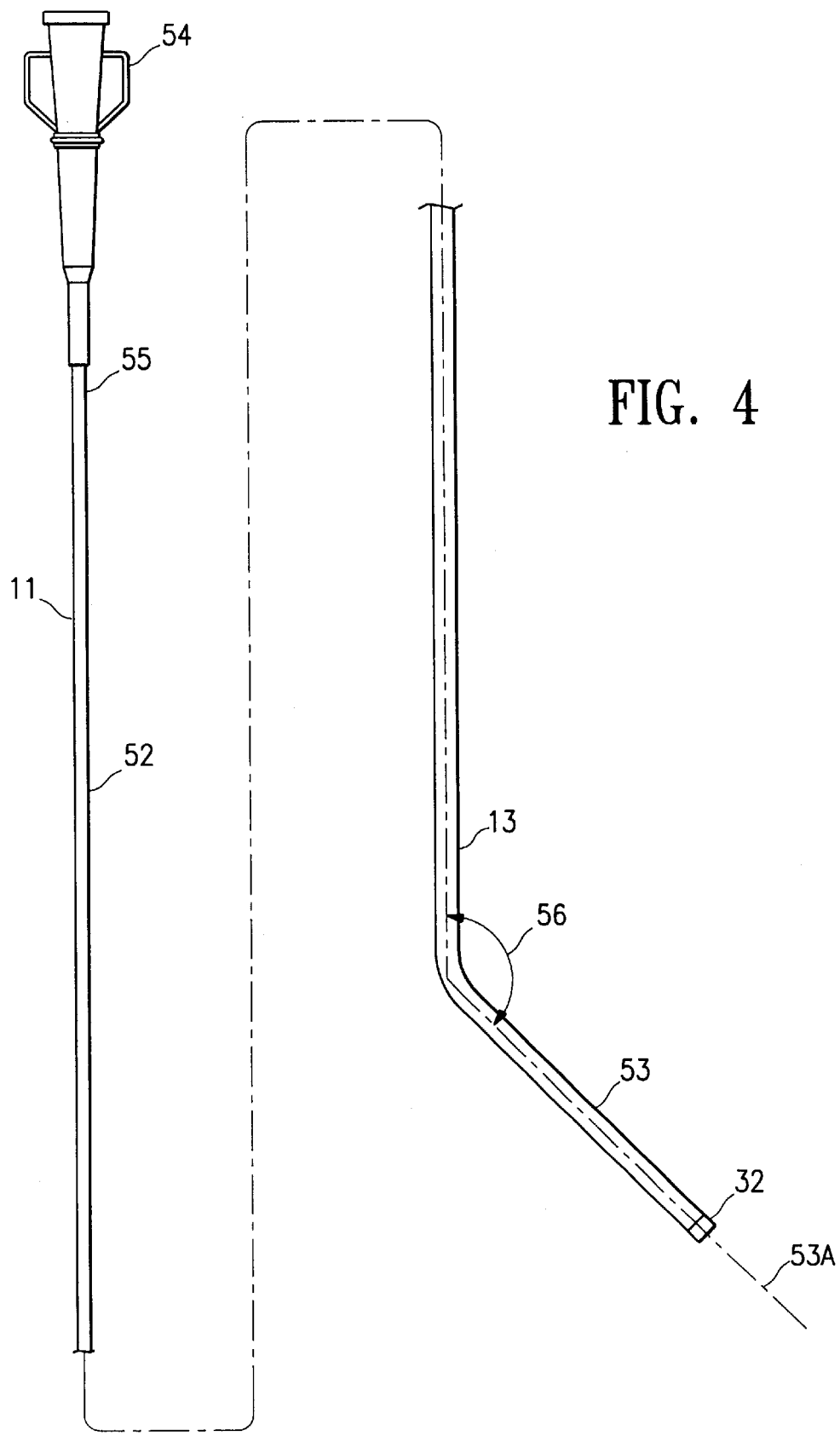
FIG. 4 is an elevational view of an alternative first delivery catheter having a shaped distal section with a single distal segment.

FIG. 4 illustrates an embodiment of the first delivery catheter 11 which has a main shaft section 52 and a shaped distal shaft section 13 with a first angled distal segment 53. The discharge axis 53A of the first delivery catheter 11 is shown extending from the first distal segment 53. The overall length of the first delivery catheter 11 is about 70 to about 130 cm, the outer diameter is about 0.1 to about 0.15 inch (2.5–3.75 mm) and the diameter of the inner lumen 45 about 0.07 to about 0.1 inch (1.8–2.5 mm). An adapter 54 is provided on a proximal end 55 of the main shaft section. In this embodiment the first angled segment 53 of the distal shaft section 13 has a length of about 1 to about 9 cm and forms an angle 56 of about 90 to about 150°, preferably about 105 to about 140°, with respect to the proximally located main shaft section 52.

Figure 5:
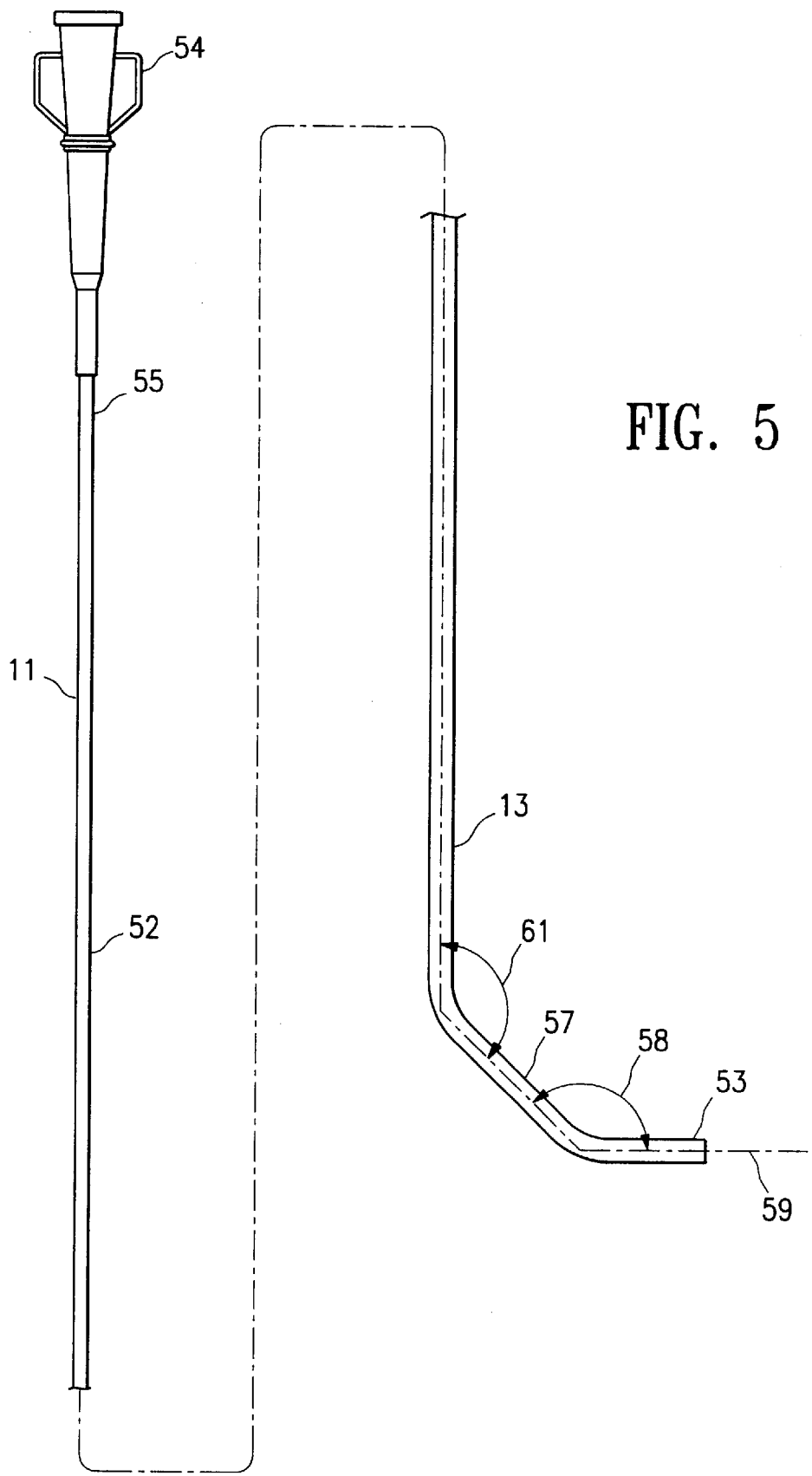
FIG. 5 is an elevational view of the first delivery catheter shown in FIG. 3.

The embodiment of the first delivery catheter 11, as shown in FIG. 5, has a shaped distal shaft section 13 with a first segment 53 and a second segment 57. The first segment 53 is shaped to be at an angle 58 with respect to the proximally adjacent second segment 57. The second segment 57 is shaped to be at an angle 61 with respect to the proximally adjacent main shaft section 52. The angle 58 the first segment 53 makes with respect to the proximally adjacent second segment 57 can be from about 90 to about 160°, preferably about 100 to about 150°. The discharge axis 59 of the first delivery catheter 11 is shown extending from the first segment 53. The angle 61 the second segment 57 makes with respect to the proximally adjacent main shaft section 52 can be from about 95 to about 165°, preferably about 100 to about 150°. The segments 53 and 57 of the distal shaft section 13 of the first delivery catheter 11 are angled to discharge the second delivery catheter 12 generally along or parallel with the longitudinal axis 44 of the left ventricle 38.

Figure 6:
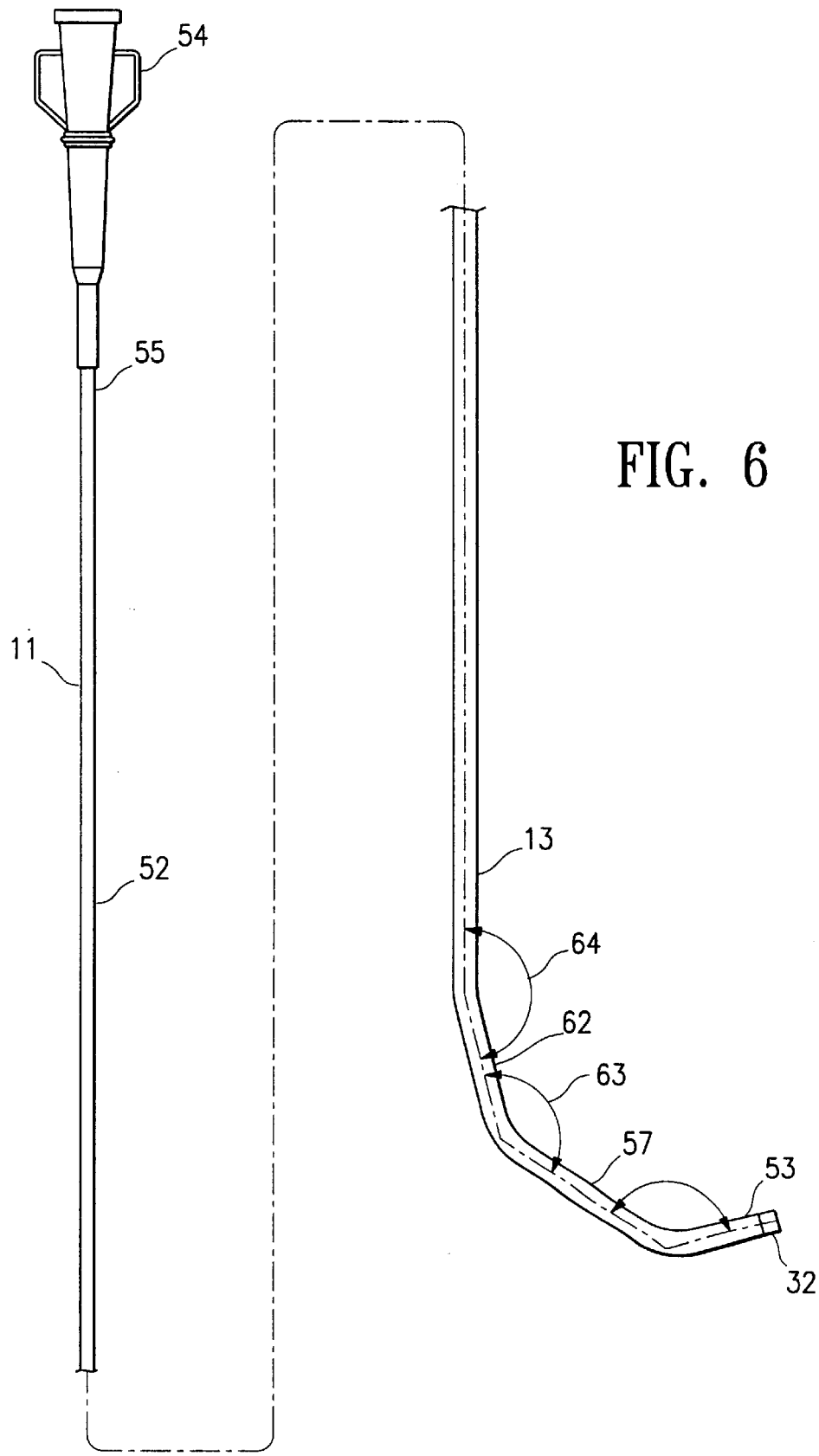
FIG. 6 is an elevational view of an alternative first delivery catheter having a shaped distal section with three segments.

Another alternative embodiment of the invention is shown in FIG. 6 where a first delivery catheter 11 is provided with a main shaft section 52 and a shaped distal shaft section 13 comprising three distal segments, a first segment 53, a second segment 57 and a third segment 62. The first segment 53 is angled with respect to the second segment 57 similarly to the embodiment described above which has two distal section segments. The angle 63 the second segment 57 makes with respect to the third segment 62 can be from about 95 to about 160°, preferably about 100 to about 135°. The third segment 62 makes an angle 64 with respect to the proximally adjacent main shaft of about 110 to about 170°, preferably about 120 to about 150°. An adapter 54 is provided on the proximal end of the main shaft section 55.

Figure 7:
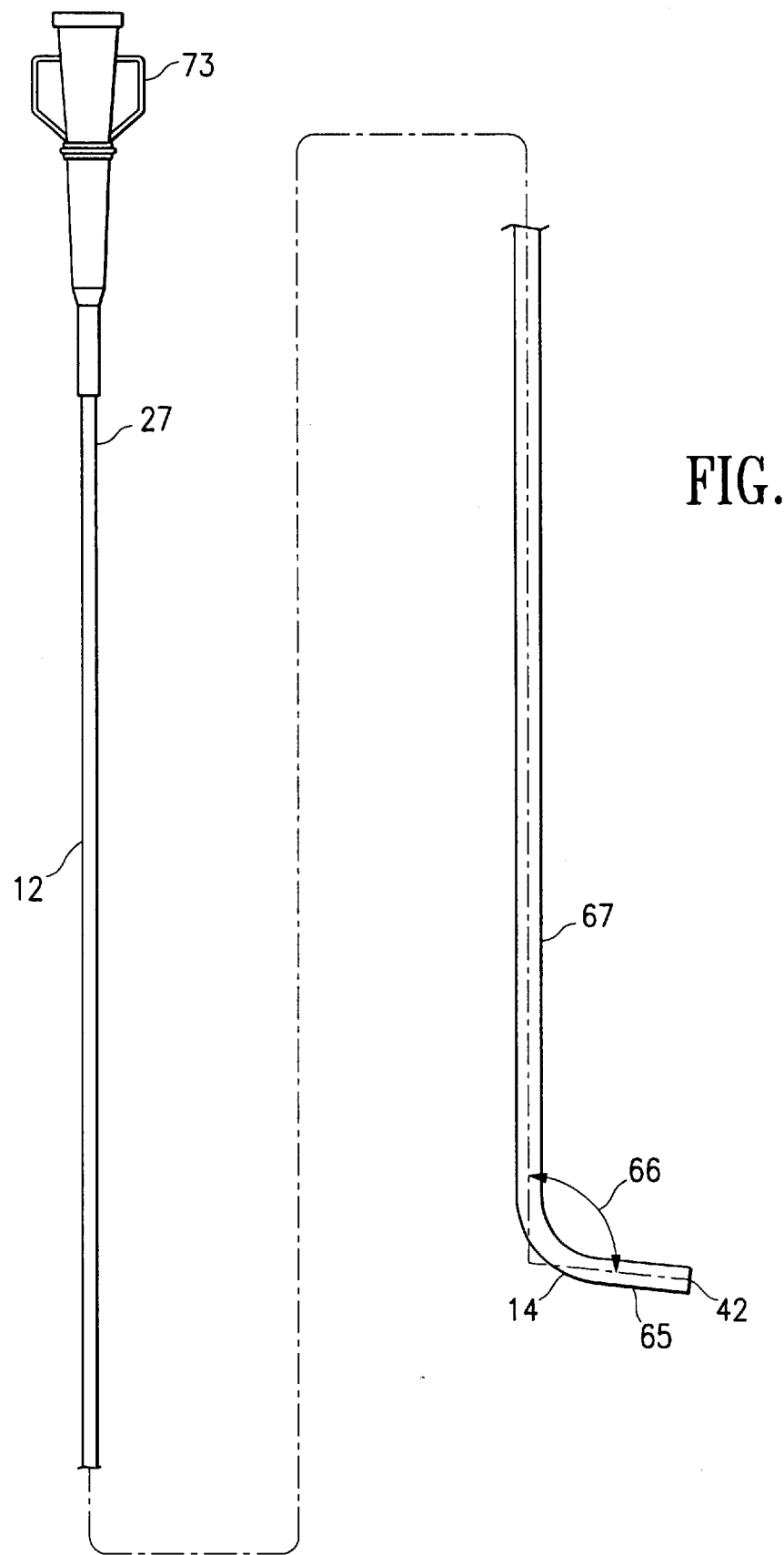
FIG. 7 is an elevational view of the second delivery catheter shown in FIG. 3.

The second delivery catheter 12, shown in FIG. 7, has a shaped distal shaft section 14 with a first segment 65 which is at an angle 66 with respect to a main shaft section 67 of the second delivery catheter 12 to ensure that the discharge axis thereof is perpendicular or near perpendicular with the region of the heart wall 41 in which the procedure is to be performed. The angle 66 of the first segment 65 of the distal shaft section of the second delivery catheter 12 with respect to the main shaft section 67 of the second delivery catheter can be from about 70 to about 150°, preferably about 90 to about 120°.

Figure 8:
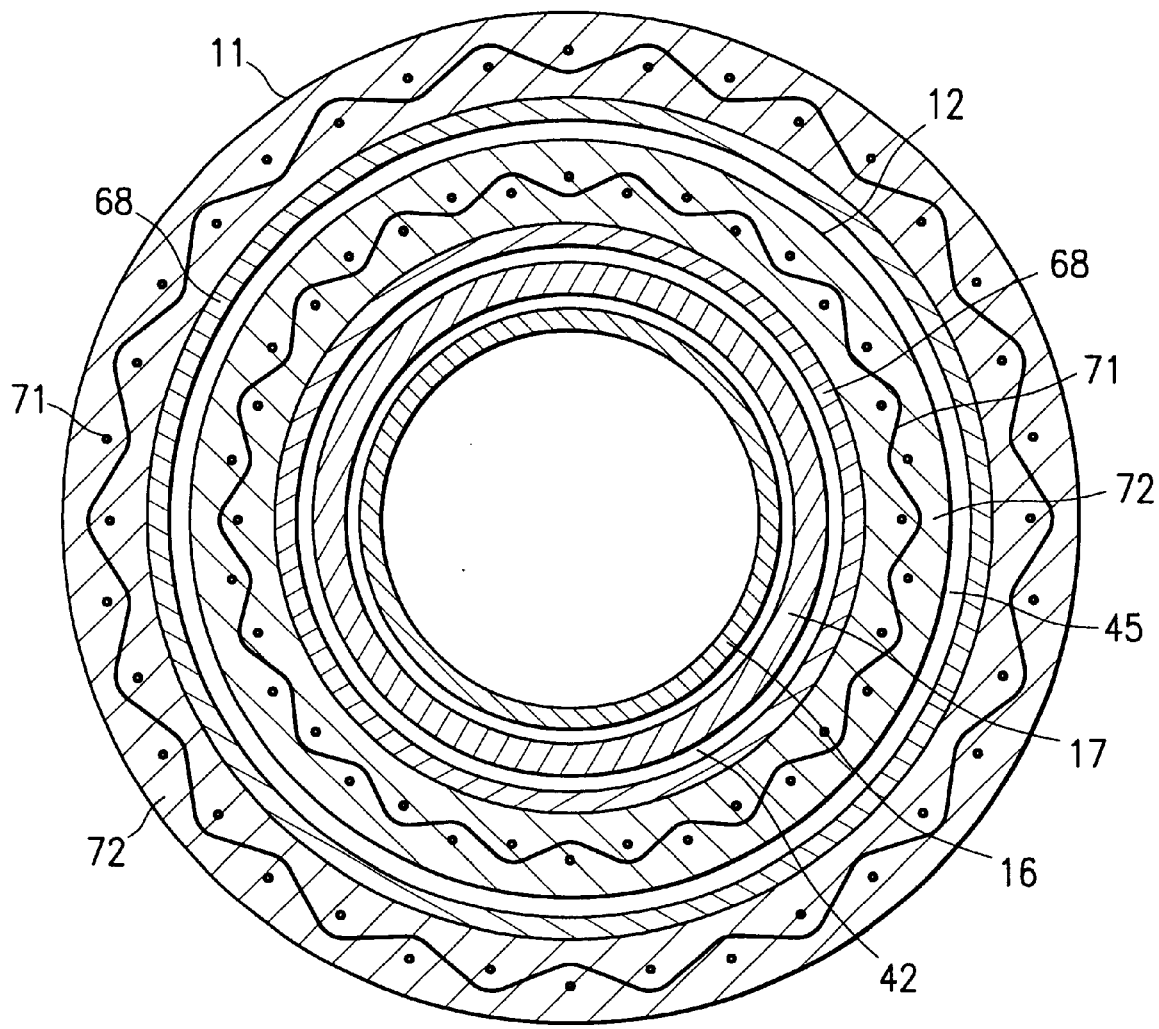
FIG. 8 is a transverse cross sectional view of the delivery catheter system shown in FIG. 3 taken along lines 8—8.

Referring to FIG. 8, the second delivery catheter 12 has a structure similar to or the same as the first delivery catheter 11 and has a lubricious lining 68, a fiber reinforcement 71 which may be braided or wound and an outer polymer jacket 72. The outer diameter of the second delivery catheter 12 is configured so that it can be readily moved longitudinally and readily rotated within the inner lumen 45 of the first delivery catheter 11 by manipulating the proximal end 27 of the second delivery catheter 12 which extends out of the patient. An adapter 73 is provided on the proximal end 27 of the second delivery catheter 12 for the introduction of therapeutic substances 25 and diagnostic devices.

The overall length of the second delivery catheter 12 is about 10 to about 40 cm longer than the first delivery catheter 11 to ensure that both the distal end 21 and the proximal end 27 of the second delivery catheter 12 can simultaneously extend out the distal end 32 and the proximal end 55 respectively of the first delivery catheter 11 so that movement of the distal end of the first delivery catheter can be effected by manipulation of the proximal end. The outer diameter of the second delivery catheter 12 is about 0.04 to less than about 0.1 inch (1–2.5 mm) and the diameter of the inner lumen 42 of the second delivery catheter is about 0.02 to about 0.07 inches (0.5–1.8 mm).

Referring again to FIG. 7, the junction between the first segment 65 and the main shaft section 67 of the second delivery catheter 12 should have a radius of curvature from about 2 to about 30 mm, preferably about 4 to about 20 mm to allow for the passage of a therapeutic or diagnostic device such as a substance delivery member 15. The radius of curvature need not be constant along the length of the curved section 14. For example, the curvature can increase progressively in the distal direction along the length of the distal shaft section 14 of the catheter.

As shown in greater detail in FIG. 8, the first delivery catheter 11 and second delivery catheter 12 may be of conventional guiding catheter construction, which can include a wall structure having a inner lubricious lining 68, a fiber reinforcement 71 in a polymer matrix which may be braided or wound and an outer jacket 72 which may be formed of suitable polymeric material in a conventional manner, e.g. extruding onto the fiber reinforcement. Suitable polymers include polyethylene, polyurethane and the like.

The strands of the fiber reinforcement 71 may be stainless steel, or other suitable high strength materials including suitable polymeric materials such as Kevlar® or Nylon. The lubricious inner liner 68 may be formed of a suitable fluoropolymer such as poly(tetrafluoro)ethylene which is sold under the trademark Teflon®. The first delivery catheter 11 may be provided with a soft, nontraumatic distal tip 32 to facilitate advancement of the catheter through a patient's vasculature without significant damage to the vessel lining. The second delivery catheter 12 may be of similar construction to that described above regarding the first delivery catheter, although the second delivery catheter 12 need not have a non-traumatic tip.

Figure 9:
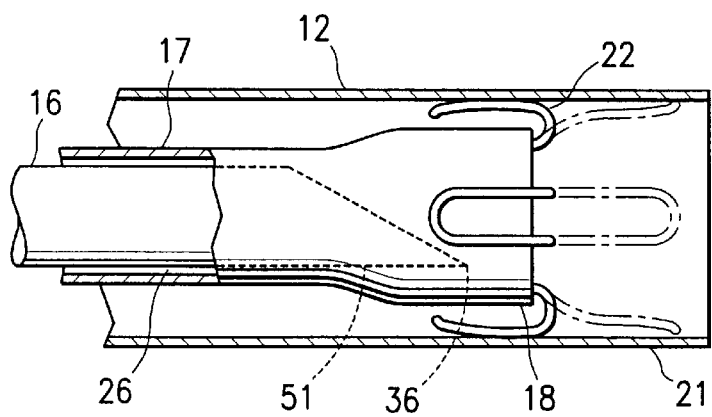
FIG. 9 is an elevational view in partial section of the distal end of the substance delivery member where the penetration limiters are in a constrained position.
Figure 10:
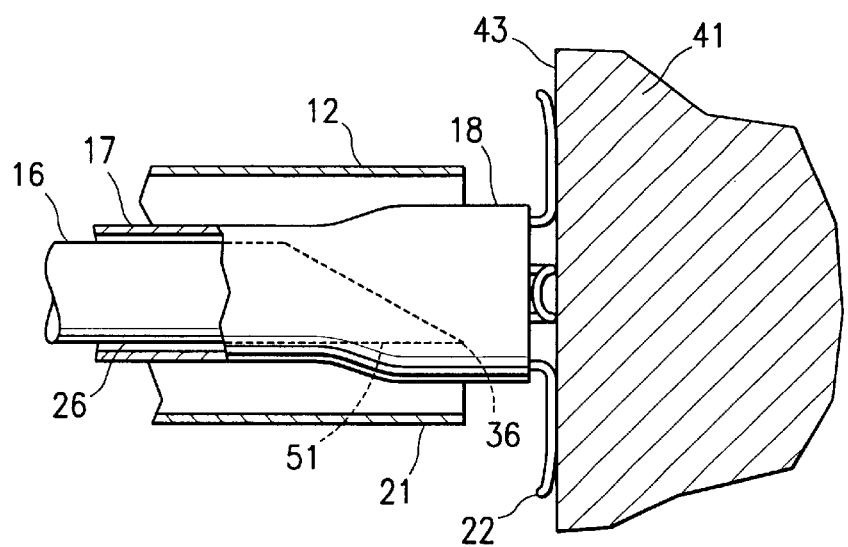
FIG. 10 is an elevational view in partial section of the distal end of the substance delivery member where the penetration limiters are in an expanded position.

In FIG. 9, it can be seen that when the distal end 21 of the second delivery catheter 12 is introduced into the vasculature, the distal end 18 of the polymer sheath 17 is preferably disposed proximally of the distal end 21 of the second delivery catheter, and the distal end 26 of the elongated cannula is in a similar position, thereby permitting a smooth introduction of the polymer sheath and elongated cannula into the second delivery catheter. The polymer sheath 17 and the second delivery catheter 12 may slide relative to one another, to either extend or retract, as necessary. The polymer sheath 17 is preferably made from a nylon or polyimide material, but may be made from any suitable polymer such as polytetraflouroethylene, sold under the trademark Teflon®, polyurethane, polypropylene, or the like. In FIG. 10, in which it is seen that the distal end 39 of the polymer sheath 17 extends beyond the distal end 21 of the second delivery catheter.

One aspect of preferred embodiments of the present invention is the provision of penetration limiters 22 on the distal end 18 of the polymer sheath 17. The provision of penetrating limiters 22 aids and enhances the use of the present invention by providing a safeguard and assurance to the user as to the position of the distal end 18 of the polymer sheath relative to the penetration of the elongated cannula 16. Additionally, the penetration limiters 22 can provide stability while the device is in place and the wall of the heart 41 continues to move. Although the present invention is useful without penetration limiters 22, it is believed that the provision of a penetration limiter or at least an enlarged diameter (not shown) at the distal end of the polymer sheath 18 will foreclose the possibility of the distal end of the polymer sheath 18 breaking the tissue surface 43.

Figure 11:
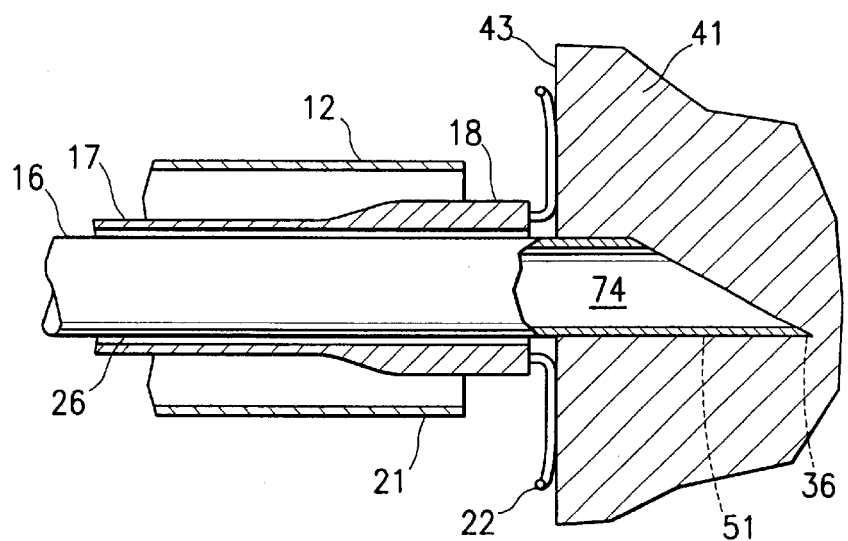
FIG. 11 is an elevational view in partial section of the distal end of the substance delivery member where the sharp distal end of the elongated cannula is extended distally beyond the distal end of the sheath of the substance delivery member.

In the illustrations shown in FIGS. 9–11, the penetration limiters 22 are most preferably Nitinol wire loops as illustrated. However, other materials will be useful for the loop construction, and penetration limiter 22 configurations other than the loops shown will also be useful. The penetration limiters 22 generally will be flexible and fold from a position permitting passage through the second delivery catheter 12 and the like and radially expand when exiting the second delivery catheter where they provide a larger distal area of contact with the tissue 43.

Finally, as seen in FIG. 11, the sharp distal tip 36 of the elongated cannula 16 will extend beyond the distal end 18 of the polymer sheath 17. It will be understood that at this point, the operator will have determined that the device is in the correct position to initiate this movement. Typically and preferably, the polymer sheath 17 will be in contact with a tissue surface 43, as supported and limited by the penetration limiters 22 described above. When in this position, a device like the elongated cannula 16 may then be moved relative to the rest of the device so that it extends below the tissue surface 43 or at least penetrates the tissue surface to permit delivery of a diagnostic or therapeutic substance 25 through its lumen 74.

Regarding the substance delivery member 15, a variety of devices are useful in addition to the illustrated elongated cannula 16. As illustrated, a simple hypodermic tube cut at an oblique angle, as is conventional in the art provides one preferred embodiment. However, it will be realized that other constructions are useful, such as blunt ends, closed ends with radial orifices, bulbous or shaped ends, tapered ends, square cut ends or ends formed into multiple spurs or barbs.

Figure 12:
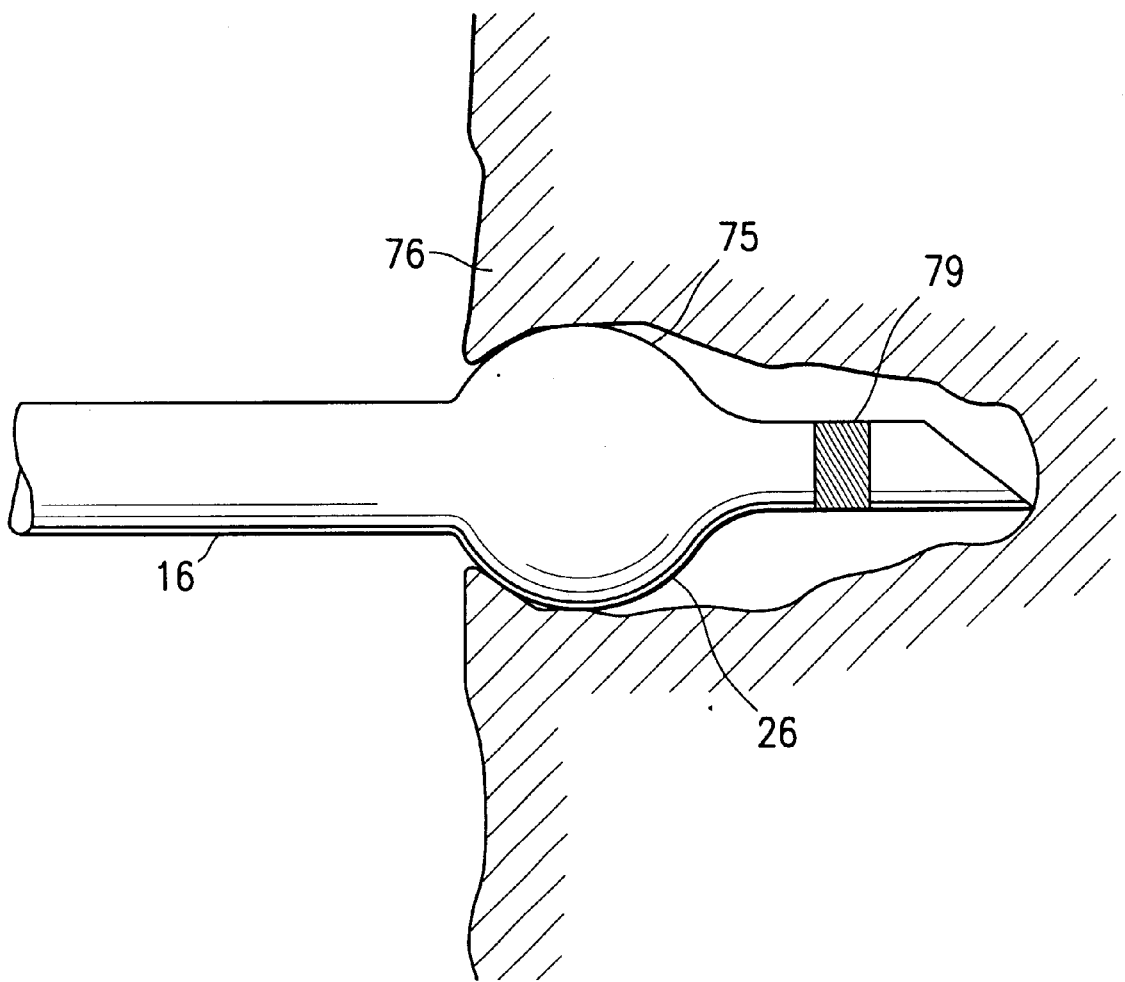
FIG. 12 is an alternative embodiment of the distal end of the elongated cannula of the substance delivery member.

FIG. 12 illustrates the distal end 26 of an elongated cannula 16 having a bulbous portion 75 which can be pushed sub-endocardially during cardiac systole. The heart tissue 76 mechanically captures the bulbous portion 75 to help maintain the position and placement of the distal end 26 of the elongated cannula 16 during substance delivery. Any and all of these constructions are contemplated for use with the present invention, so long as the distal construction chosen is effective to deliver a dose of diagnostic or therapeutic substance 25. The distal end 26 of the elongated cannula may also have a radiopaque marker 79 which is useful for positioning the distal end under flouroscopic visualization.

Referring to FIGS. 1, and 7–9, the motion of the slider 35 is most preferably integral with the motion of the sharp 36 and as such permits a 1:1 relationship between the linear motion of the slider and the distance that the sharp 36 extends. In a preferred embodiment, the slider 35 can be calibrated and provided with detents 77 such that each sub-segment of motion between detents defines a pre-determined extension of the sharp 36, e.g., one millimeter. An audible and tactile "click" provided by such arrangement will be useful to the user and assist in the effective and efficient use of the delivery catheter system 10.

In certain embodiments, however, it will be preferable to define the extension of the distal end 26 of the elongated cannula as a fixed distance. In other words, the elongated cannula 16 will move from a retracted position to an extended position, without intermediate adjustments. In an embodiment similar to that shown in FIG. 1, this will result in the slider 35 moving between a first detent 78 and a second detent 81. Alternatively, the slider 35 could be replaced with a lever or a portion of the advancement controller 33 that is squeezed so that the cannula 16 extends upon squeezing and automatically retracts. Finally, in certain embodiments, linear motion of the elongated cannula 16 would be effected with a twisting motion of a screw member which would be mechanically coupled to the elongated cannula 16. In embodiments where adjustable penetration of the distal tip 51 of the elongated cannula 16 is needed the advancement controller 33 can again be provided with detents 77 and calibrated so that each rotation between detents moves the cannula 16 a predetermined distance. Alternatively, in other embodiments, a twist or rotation of the advancement controller 33 between a first position and a second position would move the cannula 16 a predetermined distance, without control or adjustment available to the user.

Figure 13:
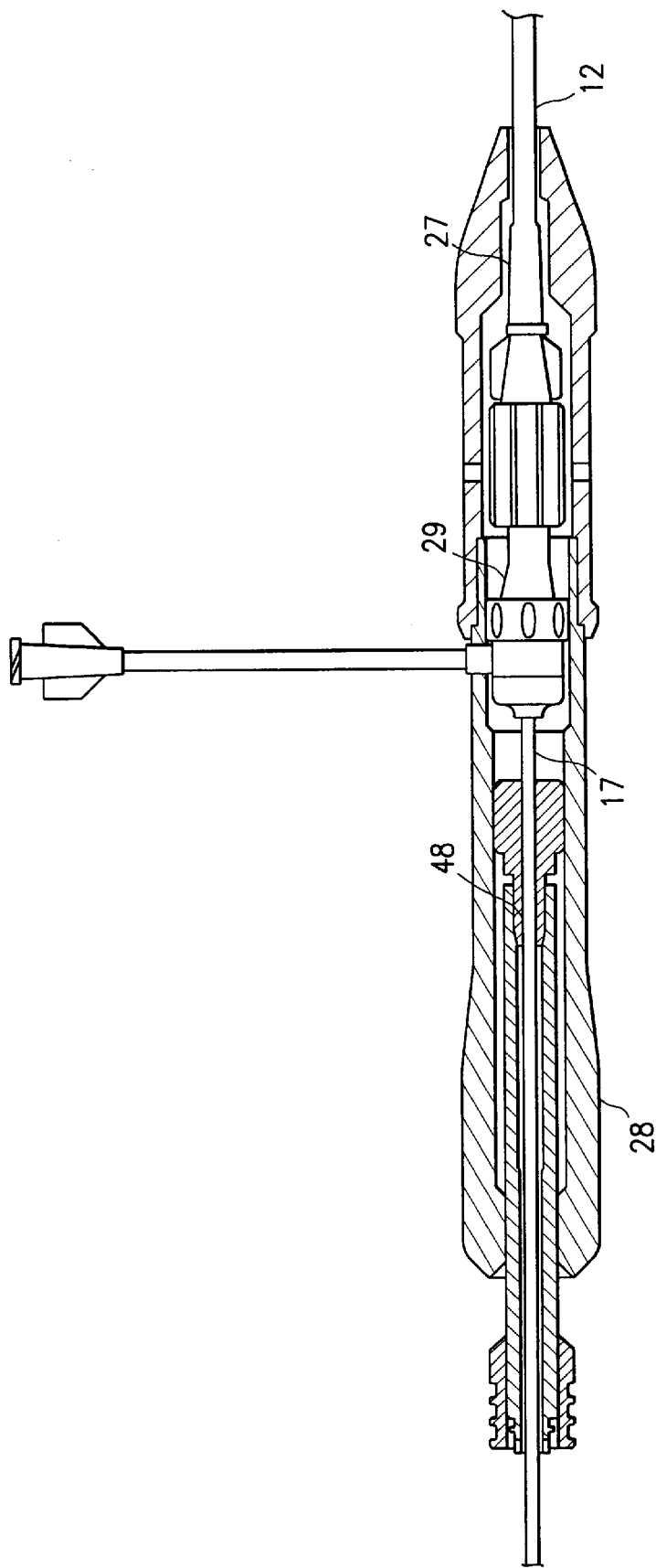
FIG. 13 is an elevational view in partial section of the proximal controller.
Figure 14:
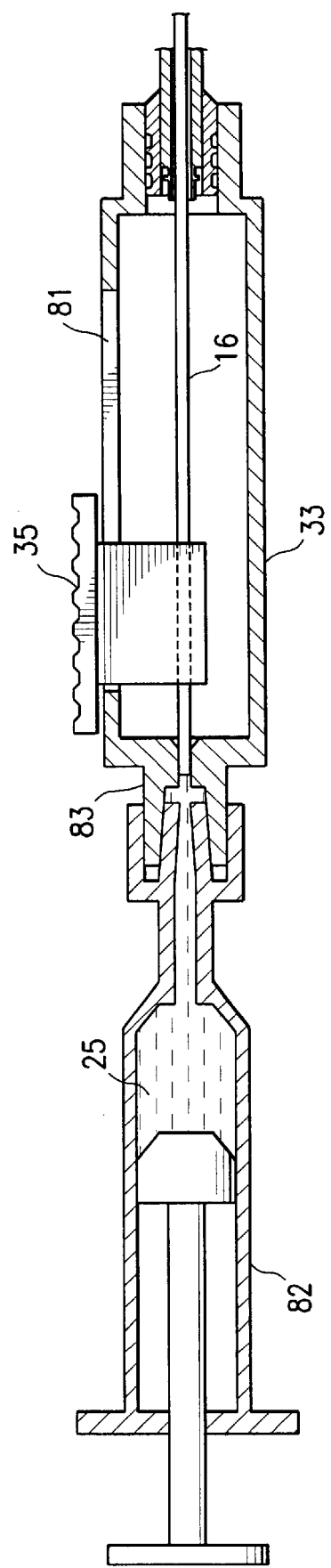
FIG. 14 is an elevational view in partial section of the advancement controller.

Referring to FIG. 13 and FIG. 14, the advancement controller 33 preferably simultaneously provides three functions, namely, polymer sheath 17 advancement, elongated cannula 16 advancement and fluid connection to the distal end 37 of the system 10. The relative motion between the advancement controller 33 and the proximal controller 28 cause the polymer sheath 17 to advance or retract relative to the second delivery catheter 12, as described above. Thus, in use, the first delivery catheter 11 and second delivery catheter 12 are guided and steered to position the distal end 37 of the catheter assembly 10 within a body cavity, and most particularly within the left ventricle 38. Next, the advancement controller 33 is moved relative to the proximal controller 28 and this action extends the polymer sheath 17 toward the tissue surface 43. Upon contact or in proximity of the tissue surface 43, a slider 35 is operated to extend an elongated cannula 16 or other substance delivery device from the distal tip of the polymer sheath 18. The range of motion of the slider 35 is constrained by the length of the slot 81 in which the slider 35 travels. After the elongated cannula 16 has been extended and is lodged in endocardial and/or myocardial tissue 41, a therapeutic or diagnostic substance 25 is injected into the tissue. In the embodiment shown, the substance injection may be effected by a simple hypodermic syringe 82 that is in fluid communication with the proximal end 83 of the advancement controller 33 via any suitable fluid-tight connection, e.g., a standard LuerLok connection. After a dose is administered, the slider 35 is used to retract the elongated cannula 16 and the advancement controller 33 is used to withdraw the polymer sheath 17, if necessary. Further details of the operation of the distal end 37 of the apparatus 10 of the present invention can be observed with reference to the sequence of views set forth in FIGS. 9–11.

Figure 15:
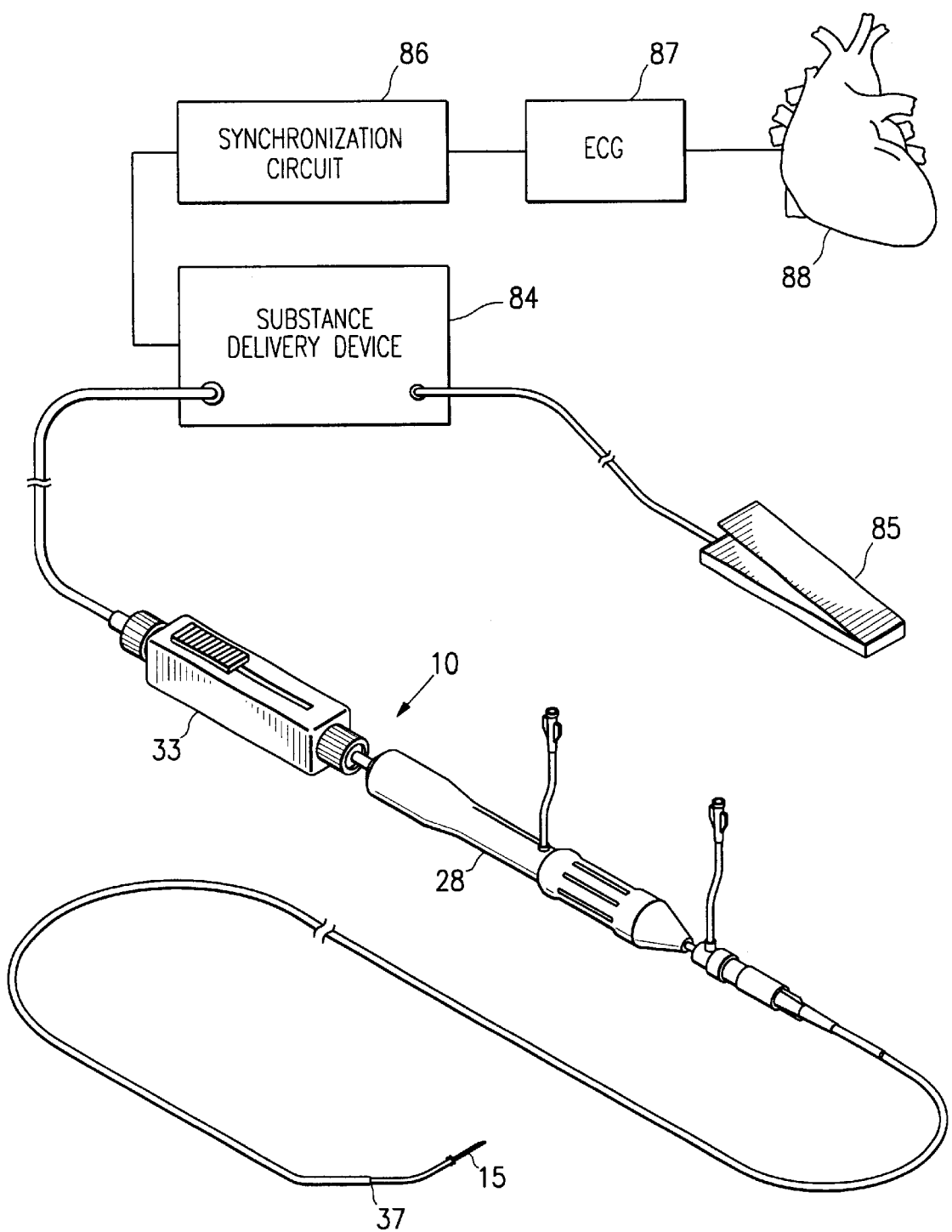
FIG. 15 is a schematic view of an alternative embodiment of the catheter delivery system which incorporates an ECG synchronizer.

Referring now to FIG. 15, an alternate embodiment of the system 10 of the present invention is shown. In this embodiment, the injector is an electronic substance delivery device 84. As shown in the art, electronic substance delivery devices 84 provide a precise, metered amount of a substance upon receiving a command. In a typical application, the signal will preferably be provided by a foot pedal 85. In some embodiments, the depressing of a foot pedal 85 will initiate a dispense cycle and a specific amount of a diagnostic or therapeutic substance 25 will be injected through the substance delivery member 15 and into the tissue. Alternately, the foot pedal 85 can be replaced by a button or trigger switch that forms part of the advancement controller 33 described above or is otherwise attached or affixed to the proximal controller 28 of the catheter. In the embodiment illustrated in FIG. 15, a further refinement is shown, in which the electronic substance delivery device 84 is connected to a synchronization circuit 86, that in turn receives a signal from an ECG 87 or other source of information about the cycle of the heart 88. In some embodiments it may be desirable to time the delivery of the substance 25 to the cardiac cycle 88, and the system 10 shown in FIG. 15 permits such timing to be accomplished. In other embodiments, the substance delivery device 15 is actuated by the extension of the elongated cannula 16, as described above, so that injection occurs upon or immediately after penetration. Alternatively, a signal for an injection, whether manual or automatic, signals a motorized extension mechanism that extends the elongated cannula 16 and follows the extension with an injection, and ultimately with an automated retraction.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A catheter system for the delivery of a therapeutic or diagnostic agent, comprising:

a) a first elongated delivery catheter which has proximal and distal ends, a port in the distal end, an inner lumen extending therein to and in fluid communication with the port in the distal end, a relatively straight main shaft section and a shaped distal shaft section having at least one segment forming an angle with respect to a proximally adjacent portion of the main shaft section;

b) a second elongated delivery catheter which is slidably and rotatably disposed within the inner lumen of the first delivery catheter, which is longer than the first delivery catheter and which has proximal and distal ends, a port in the distal end, an inner lumen, an elongated main shaft section at least a portion of which is substantially alignable with a discharge axis of the first delivery catheter and a shaped distal shaft section at least a portion of which is substantially alignable with the discharge axis of the first delivery catheter and which is configured to have a discharge axis at an angle with respect to a portion of the main shaft section thereof aligned with the discharge axis of the first delivery catheter; and c) a substance delivery member which is slidably disposed within the second delivery catheter, which has a distal extremity configured for intracorporeal delivery of a diagnostic or therapeutic substance into a patient's tissue.

2. The catheter system of claim 1 further comprising a guiding catheter configured to rotatably and slidably receive the first delivery catheter.

3. The catheter system of claim 2 wherein the first delivery catheter has a shaped distal section configured to facilitate positioning of the distal end of the second delivery catheter to a position normal to the interior wall of a patient's heart.

4. The catheter system of claim 1 wherein the substance delivery member comprises a polymer sheath disposed about an elongated cannula having a sharp distal end configured to penetrate tissue and deliver a therapeutic substance therein.

5. The catheter system of claim 4 further comprising an injector in fluid communication with a proximal end of the elongated cannula, whereby the injector injects a therapeutic or diagnostic substance into the proximal end of the cannula and out the sharp distal end, and further comprising a radiopaque marker on a distal end of the polymer sheath.

6. The catheter system of claim 5 wherein the injector is a syringe.

7. The catheter system of claim 4 wherein the elongated cannula further comprises at least one radiopaque marker to facilitate visualization of the cannula during delivery of a therapeutic or diagnostic agent.

8. The catheter system of claim 4 wherein the distal end of the elongated cannula comprises a bulbous portion which has a diameter greater than a proximally adjacent shaft section and a distally adjacent sharp distal end.

9. The catheter system of claim 4 wherein the substance delivery member includes at least one penetration limiter.

10. The catheter system of claim 9 wherein the penetration limiter is a radially expandable element.

11. The catheter system of claim 10 wherein the penetration limiter is comprised of a wire loop.

12. The catheter system of claim 1 wherein the shaped distal shaft section of the second delivery catheter is configured to have the disscharge axis at an angle of about 90° to about 120° with respect to the portion of the main shaft section thereof which is aligned with the discharge axis of the first delivery catheter.

13. The catheter system of claim 1 wherein the shaped distal section of the first delivery catheter has at least a first segment and a proximally adjacent second segment.

14. The catheter system of claim 13 wherein the first segment of the shaped distal section of the first delivery catheter is at an angle of about 95° to about 160° with respect to the proximally adjacent second segment and the second segment is at an angle of about 95° to about 150° with respect to the main shaft section proximally adjacent thereto.

15. The catheter system of claim 13 wherein the first segment of the shaped distal shaft section of the first delivery catheter is at an angle of about 100° to about 140° with respect to the adjacent second segment.

16. The catheter system of claim 13 wherein the shaped distal shaft section of the first delivery catheter includes a third segment proximally adjacent to the second segment, with the third segment at an angle with respect to the main shaft section proximal thereto of about 110° to about 170°.

17. The catheter system of claim 13 wherein the shaped distal shaft section of the first delivery catheter includes a third segment proximally adjacent to the second segment, with the third segment at an angle with respect to the main shaft section proximal thereto of about 120° to about 150°.

18. The catheter system of claim 13 wherein the first segment of the shaped distal shaft section of the first delivery catheter has a length of about 0.5 to about 5 cm.

19. The catheter system of claim 13 wherein the first segment of the shaped distal shaft section of the first delivery catheter has a length of about 1 to about 4 cm.

20. The catheter system of claim 13 wherein the second segment of the shaped distal shaft section of the first delivery catheter has a length of about 0.5 to about 5 cm.

21. The catheter system of claim 13 wherein the second segment of the shaped distal shaft section of the first delivery catheter has a length of about 1 to about 4 cm.

22. The catheter system of claim 17 wherein the third segment of the shaped distal shaft section of the first delivery catheter has a length of about 1 to about 5 cm.

23. The catheter system of claim 17 wherein the third segment of the shaped distal shaft section of the first delivery catheter has a length of about 2 to about 4 cm.

24. The catheter system of claim 13 wherein the length of the shaped distal shaft section of the first delivery catheter is about 2 to about 8 cm.

25. The catheter system of claim 13 wherein the length of the shaped distal shaft section of the first delivery catheter is about 4 to about 7 cm.

26. The catheter system of claim 1 wherein the shaped distal section of the first delivery catheter has a single segment.

27. The catheter system of claim 26 wherein the single segment of the shaped distal section is at an angle of about 95° to about 160° with respect to the proximally adjacent main shaft section.

28. The catheter system of claim 26 wherein the single segment of the shaped distal section is at an angle of about 100° to about 140° with respect to the proximally adjacent main shaft section.

29. The catheter system of claim 26 wherein the single segment of the shaped distal section has a length of about 3 to about 8 cm.

30. The catheter system of claim 26 wherein the single segment of the shaped distal section of the first delivery catheter has a length of about 4 to about 6 cm.

31. The catheter system of claim 26 wherein the single segment has a length of about 0.5 to about 5 cm.

32. The catheter system of claim 26 wherein the single segment of the shaped distal section of the first delivery catheter has a length of about 1 to about 4 cm.

33. The catheter system of claim 13 wherein the shaped distal section of the first delivery catheter has a third segment which is proximally adjacent to the second segment.

34. The catheter system of claim 33 wherein the third segment has a length of about 1 to about 5 cm.

35. The catheter system of claim 33 wherein the third segment has a length of about 2 to about 4 cm.

36. The catheter system of claim 33 wherein the length of the shaped distal section is about 2 to about 8 cm.

37. The catheter system of claim 33 wherein the length of the shaped distal section is about 4 to about 7 cm.

38. A method for performing a therapeutic or diagnostic procedure in a region of a wall of a patient's heart defining a heart chamber, comprising:
   a) introducing into a peripheral artery of the patient a delivery catheter system which includes;
      a first delivery catheter having an elongated shaft which has proximal and distal ends, a port in the distal end and an inner lumen extending therein to and in fluid communication with the port in the distal end, a relatively straight main shaft section and a shaped distal shaft section forming an angle with respect to a proximally adjacent portion of the main shaft section so that the distal section has a discharge axis which is generally aligned with or parallel to longitudinal axis of the patient's left ventricle; and
      a second elongated delivery catheter which is slidably and rotatably disposed within the inner lumen of the first delivery catheter, which is longer than the first delivery catheter and which has proximal and distal ends, a port in the distal end, an inner lumen extending to and in fluid communication with the port in the distal end, an elongated main shaft section and a shaped distal shaft section configured to have a discharge axis at an angle of about 80° to about 135° with respect to a portion of the main shaft section of the second delivery catheter which is substantially aligned with the discharge axis of the first delivery catheter so as to be normal to said region of the heart wall, and
      a substance delivery member having a distal extremity which is configured to extend beyond the distal end of the second delivery catheter configured to deliver a diagnostic or therapeutic substance to the wall of the patient's heart;
   b) advancing at least the first delivery catheter through the patient's arterial system until the shaped distal shaft section of the first delivery catheter extends into the patient's left ventricle substantially aligned with or parallel to the longitudinal axis of the left ventricle;
   c) advancing the second delivery catheter within the first delivery catheter until at least a portion of the shaped distal shaft section of the second delivery catheter extends out the port in the distal end of the first delivery catheter; and
   d) positioning the second delivery catheter within the left ventricle so that the shaped distal shaft section thereof is substantially normal to the region of the heart wall where the procedure is to be performed; and;
   e) extending the distal extremity of the substance delivery member until the distal end thereof is in a position to deliver a diagnostic or therapeutic substance into the patient's heart wall.

39. The method of claim 38 wherein the delivery catheter system further comprises an intermediate delivery catheter having a proximal and distal end and which is slidably and rotatably received by the first delivery catheter and which slidably and rotatably receives the second delivery catheter, and further comprising the step of advancing the intermediate delivery catheter through the first delivery catheter after it has been positioned within the patient's left ventricle, and then advancing the second delivery catheter within the intermediate delivery catheter until a portion of the shaped distal shaft section of the second delivery catheter extends out of the distal end of the intermediate delivery catheter.

40. The method of claim 38 wherein the substance delivery member is an elongated cannula with a distal extremity and wherein the distal extremity is extended out of the port in the distal end of the second delivery catheter until the distal extremity penetrates the desired region of the patient's heart wall.

41. The method of claim 40 wherein the substance delivery member further comprises a polymer sheath slidably disposed about the elongated cannula and slidably disposed within the second delivery catheter.

42. The method of claim 40 including the step of activating the substance delivery member so as to perform the procedure at said region.

43. A method for developing neovasculogenesis within a region of a patient's heart wall defining a heart chamber, comprising:
   a) advancing a first delivery catheter through the patient's vasculature until a distal section of the first delivery catheter extends into the patient's heart chamber and is substantially aligned with or parallel to a longitudinal axis of the heart chamber;
   b) advancing a second delivery catheter through an inner lumen of the first delivery catheter until a shaped distal section of the second delivery catheter extends out of the distal end of the first delivery catheter;
   c) adjusting the position of the second delivery catheter until a discharge axis of the second delivery catheter is substantially normal to the region of the heart wall in which the neovasculogenesis is to be developed;
   d) advancing a substance delivery member from the distal end of the second delivery catheter until the distal end of the substance delivery member penetrates into the desired region of the patient's heart wall; and
   e) delivering an neovasculogenesis agent through the distal extremity of the substance delivery member within the heart wall to develop angiogenesis therein.

44. The method of claim 43 wherein the substance delivery member is an elongated cannula.

45. A delivery catheter system for delivering a therapeutic substance in a desired region of a wall of a patient's heart, comprising:
   a) a first delivery catheter which has proximal and distal ends, a port in the distal end, an inner lumen extending to and in communication with the port in the distal end, an elongated proximal section with a longitudinal axis and a distal section which is shorter than the proximal section, with the distal shaft section shaped so as to be directed toward the desired region of the heart wall and which includes a proximal portion having a longitudinal axis and extending at an angle of about 50° to about 130° from the longitudinal axis of the proximal section and a distal portion which is at an angle of about 50° to about 130° from the longitudinal axis of the proximal portion; and
   b) a substance delivery member slidably disposed within the inner lumen of the first delivery catheter and configured to have a distal end which extends out of the port in the distal end of the first delivery catheter.

46. A delivery catheter system for percutaneously delivering diagnostic or therapeutic substances into a patient's heart comprising:

a) a first delivery catheter which has proximal and distal ends, a port in the distal end, an inner lumen extending therein to and in communication with the port in the distal end, a main shaft portion and a distal shaft portion which is configured to extend at least into the patient's ascending aorta and having a discharge axis; and b) a second delivery catheter which is slidably disposed within the inner lumen of the first delivery catheter, which is longer than the first delivery catheter, and which has proximal and distal ends, a port in the distal end, an inner lumen extending therein to and in fluid communication with the port in the distal end of the second delivery catheter and a distal extremity having discharge axis at an angle of at least 30° from the discharge axis of the first catheter; and c) a substance delivery member which is slidably disposed within the inner lumen of the second delivery catheter and which is configured to extend out the port in the distal end of the second delivery catheter to engage a portion of a patient's heart.

* * * * *